United States Patent
Stein et al.

(10) Patent No.: US 8,516,907 B2
(45) Date of Patent: Aug. 27, 2013

(54) LOAD SENSING PLATFORM FOR MEASURING A PARAMETER OF THE MUSCULAR-SKELETAL SYSTEM

(75) Inventors: Marc Stein, Chandler, AZ (US); James Ellis, Tempe, AZ (US)

(73) Assignee: Orthosensor Inc., Sunrise, FL (US)

(*) Notice: Subject to any disclaimer, the term of this patent is extended or adjusted under 35 U.S.C. 154(b) by 450 days.

(21) Appl. No.: 12/825,753

(22) Filed: Jun. 29, 2010

(65) Prior Publication Data

US 2010/0326210 A1     Dec. 30, 2010

Related U.S. Application Data

(60) Provisional application No. 61/221,867, filed on Jun. 30, 2009, provisional application No. 61/221,761, filed on Jun. 30, 2009, provisional application No. 61/221,767, filed on Jun. 30, 2009, provisional application No. 61/221,779, filed on Jun. 30, 2009, provisional application No. 61/221,788, filed on Jun. 30, 2009, provisional application No. 61/221,793, filed on Jun. 30, 2009, provisional application No. 61/221,801, filed on Jun. 30, 2009, provisional application No. 61/221,808, filed on Jun. 30, 2009, provisional application No. 61/221,817, filed on Jun. 30, 2009, provisional application No. 61/221,874, filed on Jun. 30, 2009, provisional application No. 61/221,879, filed on Jun. 30, 2009, provisional application No. 61/221,881, filed on Jun. 30, 2009, provisional application No. 61/221,886, filed on Jun. 30, 2009, provisional application No. 61/221,889, filed on Jun. 30, 2009, provisional application No. 61/221,894, filed on Jun. 30, 2009, provisional application No. 61/221,901, filed on Jun. 30, 2009, provisional application No. 61/221,909, filed on Jun. 30, 2009, provisional application No. 61/221,916, filed on Jun. 30, 2009, provisional application No. 61/221,923, filed on Jun. 30, 2009, provisional application No. 61/221,929, filed on Jun. 30, 2009.

(51) Int. Cl.
    *G01L 1/04*         (2006.01)

(52) U.S. Cl.
    USPC .................................................... 73/862.636

(58) Field of Classification Search
    USPC .................................................... 73/862.636
    See application file for complete search history.

(56) References Cited

U.S. PATENT DOCUMENTS

| | | |
|---|---|---|
| 5,197,488 A | 3/1993 | Kovacevic |
| 5,470,354 A | 11/1995 | Hershberger et al. |
| 5,683,396 A | 11/1997 | Tokish et al. |
| 5,688,279 A | 11/1997 | McNulty et al. |

(Continued)

*Primary Examiner* — Lisa Caputo
*Assistant Examiner* — Octavia D. Hollington

(57) ABSTRACT

A load sensing platform (121) is disclosed for capturing a transit time, phase, or frequency of energy waves propagating through a medium that measures a parameter of the muscular-skeletal system. The load sensing platform (121) comprises a sensing assemblage (1), substrates (702, 704, and 706), springs (315), spring posts (708), and spring retainers (710). The sensing assemblage (1) comprises a stack of a transducer (5), waveguide (3), and transducer (6). A parameter is applied to the contact surfaces (8) of the load sensing platform (121). The sensing assemblage (1) measures changes in dimension due to the parameter. Position of the applied parameter can be measured by using more than one sensing assemblage (1). The springs (315) couple to the substrates (702, 704) providing mechanical support and to prevent cantilevering. The spring posts (708) and spring retainers (710) maintain the springs (315) at predetermined locations in the load sensing platform (121).

16 Claims, 7 Drawing Sheets

(56) References Cited

U.S. PATENT DOCUMENTS

| | | |
|---|---|---|
| 5,871,018 A | 2/1999 | Delp et al. |
| 5,900,592 A * | 5/1999 | Sohns et al. ............... 177/210 R |
| 6,171,252 B1 | 1/2001 | Roberts |
| 6,245,109 B1 | 6/2001 | Mendes et al. |
| 6,515,593 B1 * | 2/2003 | Stark et al. ............... 340/870.07 |
| 6,583,630 B2 | 6/2003 | Mendes et al. |
| 6,621,278 B2 | 9/2003 | Ariav |
| 6,701,174 B1 | 3/2004 | Krause et al. |
| 6,714,763 B2 | 3/2004 | Hamel et al. |
| 6,821,299 B2 | 11/2004 | Kirking et al. |
| 6,856,141 B2 | 2/2005 | Ariav |
| 7,001,346 B2 | 2/2006 | White |
| 7,097,662 B2 | 8/2006 | Evans et al. |
| 7,195,645 B2 | 3/2007 | Disilvestro et al. |
| 7,256,695 B2 | 8/2007 | Hamel et al. |
| 7,295,724 B2 | 11/2007 | Wang et al. |
| 7,442,196 B2 | 10/2008 | Fisher et al. |
| 7,575,602 B2 | 8/2009 | Amirouche et al. |
| 7,578,821 B2 | 8/2009 | Fisher et al. |
| 7,587,945 B2 | 9/2009 | Crottet et al. |
| 7,615,055 B2 | 10/2009 | DiSilvestro |
| 7,632,283 B2 | 12/2009 | Heldreth |
| 2002/0029784 A1 | 3/2002 | Stark et al. |
| 2005/0020941 A1 | 1/2005 | Tarabichi |
| 2006/0058798 A1 | 3/2006 | Roman et al. |
| 2006/0232408 A1 | 10/2006 | Nyez et al. |
| 2006/0271112 A1 | 11/2006 | Martinson et al. |
| 2007/0219561 A1 | 9/2007 | Lavallee et al. |
| 2007/0272747 A1 | 11/2007 | Woods et al. |

\* cited by examiner

LOAD SENSING PLATFORM FOR MEASURING A PARAMETER OF THE MUSCULAR-SKELETAL SYSTEM

CROSS-REFERENCE TO RELATED APPLICATIONS

This application claims the priority benefit of U.S. provisional patent application Nos. 61/221,761, 61/221,767, 61/221,779, 61/221,788, 61/221,793, 61/221,801, 61/221,808, 61/221,817, 61/221,867, 61/221,874, 61/221,879, 61/221,881, 61/221,886, 61/221,889, 61/221,894, 61/221,901, 61/221,909, 61/221,916, 61/221,923, and 61/221,929 all filed 30 Jun. 2009; the disclosures of which are hereby incorporated herein by reference in their entirety.

FIELD

The present invention pertains generally to measurement of physical parameters, and particularly to, but not exclusively to, real-time measurement of load, force, and pressure.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTION OF THE DRAWINGS

Various features of the system are set forth with particularity in the appended claims. The embodiments herein, can be understood by reference to the following description, taken in conjunction with the accompanying drawings, in which:

DETAILED DESCRIPTION

Figure 1:
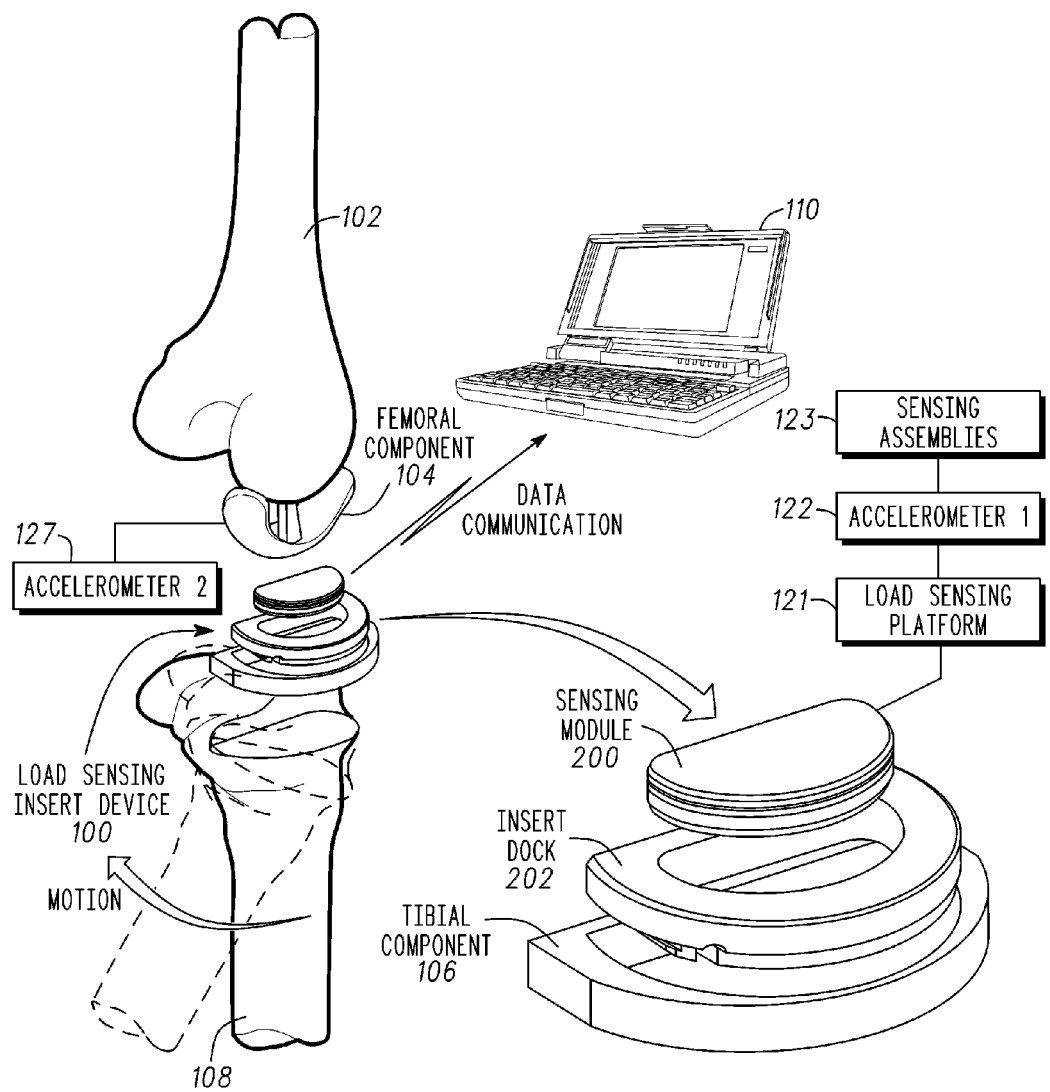
FIG. 1 is an illustration of a load sensing insert device placed in contact between a femur and a tibia for measuring a parameter in accordance with an exemplary embodiment.

Embodiments of the invention are broadly directed to measurement of physical parameters, and more particularly, to real-time measurement of load, force, pressure, displacement, density, localized temperature, or viscosity by changes in the transit time of ultrasonic waves propagating within waveguides integrated within sensing platforms placed on or within a body, instrument, appliance, vehicle, equipment, or other physical system.

In all of the examples illustrated and discussed herein, any specific materials, temperatures, times, energies, etc. for process steps or specific structure implementations should be interpreted to illustrative only and non-limiting. Processes, techniques, apparatus, and materials as known by one of ordinary skill in the art may not be discussed in detail but are intended to be part of an enabling description where appropriate.

Note that similar reference numerals and letters refer to similar items in the following figures. In some cases, numbers from prior illustrations will not be placed on subsequent figures for purposes of clarity. In general, it should be assumed that structures not identified in a figure are the same as previous prior figures.

One embodiment is a load sensing platform that employs a combination of two or more load bearing surfaces incorporating features for contacting external objects, energy transducer or transducers, compressible energy propagating structure or structures or media, and spring or springs or other means of elastic support, to measure force or pressure external to the load sensing platform or displacement produced by contact with an external object. A position of the center or focal point (or locus or centroid) of the applied load, force, pressure, or external contact on the load bearing or contacting surface or surfaces of the load sensing platform can be determined. The centroid or barycenter is considered the average of all points, weighted by the local density. In fluid mechanics, the force density has the physical dimensions of force per unit volume Force, pressure, displacement, density, or viscosity is detected by controlled compression or displacement of the compressible energy propagating structure or structures or media. The compression or displacement of the compressible energy propagating structure or structures or media is accurately controlled by the action of the spring or springs or other means of elastic support positioned in conjunction with the compressible energy propagating structure or structures or media between the load bearing or contacting surfaces. Changes in compression or displacement of the compressible energy propagating structure or structures or media alter their physical length and may be detected by changes in transit time of energy pulses or waves propagating therein. The center or focal point (or locus or centroid) of the applied force, pressure, displacement, density, or viscosity on the load bearing or contacting surfaces may be determined by combining measurements taken with a combination of assemblages of energy transducers and compressible energy propagating structure or structures or media.

For clarity, the remainder of the description focuses on a specific form of energy and medium of propagation. Ultrasound energy pulses or waves, the emission of ultrasound pulses or waves by ultrasound resonators or transducers, transmitted through ultrasound waveguides, and detected by ultrasound resonators or transducers will be used in the following discussion and examples of embodiments of the present invention as examples of energy pulses, waves, and propagation structures and media.

FIG. 1 is an illustration of a load sensing insert device 100 placed in contact between a femur 102 and a tibia 108 for measuring a parameter in accordance with an exemplary embodiment. In general, load sensing insert device 100 is placed in contact with or in proximity to the muscular-skeletal system to measure a parameter. In a non-limiting example, device 100 is used to measure a parameter of a muscular-skeletal system during a procedure such as an installation of an artificial joint. As illustrated, the device 100 in this example can intra-operatively assess a load on prosthetic components during the surgical procedure. It can collect load data for real-time viewing of the load forces over various applied loads and angles of flexion. It can measure the level and distribution of load at various points on the prosthetic component and transmit the measured load data by way of data communication to a receiver station 110 for permitting visualization. This can aid the surgeon in making any adjustments needed to achieve optimal joint balancing.

The load sensing insert device 100, in one embodiment, comprises a load sensing platform 121, an accelerometer 122, and sensing assemblies 123. This permits the sensing device 100 to assess a total load on the prosthetic components when it is moving; it accounts for forces due to gravity and motion. In one embodiment, load sensing platform 121 includes two or more load bearing surfaces, at least one energy transducer, at least one compressible energy propagating structure, and at least one member for elastic support. The accelerometer 122 can measure acceleration. Acceleration can occur when the load sensing device 100 is moved or put in motion. Accelerometer 122 can sense orientation, vibration, and impact. In another embodiment, the femoral component 104 can similarly include an accelerometer 127, which by way of a communication interface to the load sensing insert device 100, can provide reference position and acceleration data to determine an exact angular relationship between the femur and tibia. The sensing assemblies 123 can reveal changes in length or compression of the energy propagating structure or structures by way of the energy transducer or transducers. Together the load sensing platform 121, accelerometer 122 (and in certain cases accelerometer 127), and sensing assemblies 123 measure force or pressure external to the load sensing platform or displacement produced by contact with the prosthetic components.

Incorporating data from the accelerometer 122 with data from the other sensing components 121 and 123 assures accurate measurement of the applied load, force, pressure, or displacement by enabling computation of adjustments to offset this external motion. This capability can be required in situations wherein the body, instrument, appliance, vehicle, equipment, or other physical system, is itself operating or moving during sensing of load, pressure, or displacement. This capability can also be required in situations wherein the body, instrument, appliance, vehicle, equipment, or other physical system, is causing the portion of the body, instrument, appliance, vehicle, equipment, or other physical system being measured to be in motion during sensing of load, pressure, or displacement.

The accelerometer 122 can operate singly, as an integrated unit with the load sensing platform 121, and/or as an integrated unit with the sensing assemblies 123. Integrating one or more accelerometers 122 within the sensing assemblies 123 to determine position, attitude, movement, or acceleration of sensing assemblies 123 enables augmentation of presentation of data to accurately identify, but not limited to, orientation or spatial distribution of load, force, pressure, displacement, density, or viscosity, or localized temperature by controlling the load and position sensing assemblages to measure the parameter or parameters of interest relative to specific orientation, alignment, direction, or position as well as movement, rotation, or acceleration along any axis or combination of axes. Measurement of the parameter or parameters of interest may also be made relative to the earth's surface and thus enable computation and presentation of spatial distributions of the measured parameter or parameters relative to this frame of reference.

In one embodiment, the accelerometer 122 includes direct current (DC) sensitivity to measure static gravitational pull with load and position sensing assemblies to enable capture of, but not limited to, distributions of load, force, pressure, displacement, movement, rotation, or acceleration by controlling the sensing assemblies to measure the parameter or parameters of interest relative to orientations with respect to the earths surface or center and thus enable computation and presentation of spatial distributions of the measured parameter or parameters relative to this frame of reference.

Embodiments of device 100 are broadly directed to measurement of physical parameters, and more particularly, to evaluating changes in the transit time of a pulsed energy wave propagating through a medium. In-situ measurements during orthopedic joint implant surgery would be of substantial benefit to verify an implant is in balance and under appropriate loading or tension. In one embodiment, the instrument is similar to and operates familiarly with other instruments currently used by surgeons. This will increase acceptance and reduce the adoption cycle for a new technology. The measurements will allow the surgeon to ensure that the implanted components are installed within predetermined ranges that maximize the working life of the joint prosthesis and reduce costly revisions. Providing quantitative measurement and assessment of the procedure using real-time data will produce results that are more consistent. A further issue is that there is little or no implant data generated from the implant surgery, post-operatively, and long term. Device 100 can provide implant status data to the orthopedic manufacturers and surgeons. Moreover, data generated by direct measurement of the implanted joint itself would greatly improve the knowledge of implanted joint operation and joint wear thereby leading to improved design and materials.

In at least one exemplary embodiment, an energy pulse is directed within one or more waveguides in device 100 by way of pulse mode operations and pulse shaping. The waveguide is a conduit that directs the energy pulse in a predetermined direction. The energy pulse is typically confined within the waveguide. In one embodiment, the waveguide comprises a polymer material. For example, urethane or polyethylene are polymers suitable for forming a waveguide. The polymer waveguide can be compressed and has little or no hysteresis in the system. Alternatively, the energy pulse can be directed through the muscular-skeletal system. In one embodiment, the energy pulse is directed through bone of the muscular-skeletal system to measure bone density. A transit time of an energy pulse is related to the material properties of a medium through which it traverses. This relationship is used to generate accurate measurements of parameters such as distance, weight, strain, pressure, wear, vibration, viscosity, and density to name but a few.

A surgeon can affix a femoral prosthetic component 104 to the femur 102 and a tibial prosthetic component 106 to the patient's tibia 108. The tibial prosthetic component 106 can be a tray or plate affixed to a planarized proximal end of the tibia 108. The load sensing insert device 100 is fitted between the plate of the tibial prosthetic component 106 and the femoral prosthetic component 104. These three prosthetic components (104, 100 and 106) enable the prostheses to emulate the functioning of a natural knee joint. It can measure loads at various points (or locations) on the femoral prosthetic component 104 in view of the position and acceleration data and transmit the measured data to a receiving station 110. The receiving station 110 can include data processing, storage, or display, or combination thereof and provide real time graphical representation of the level and distribution of the load when the load sensing device 100 is stationary and in motion.

A proximal end of tibia 108 is prepared to receive tibial prosthetic component 106. Tibial prosthetic component 106 is a support structure that is fastened to the proximal end of the tibia and is usually made of a metal or metal alloy. The tibial prosthetic component 106 also retains the insert in a fixed position with respect to tibia 108. The insert is fitted between femoral prosthetic component 104 and tibial prosthetic component 106. The insert has at least one bearing surface that is in contact with at least condyle surface of femoral prosthetic component 104. The condyle surface can move in relation to the bearing surface of the insert such that the lower leg can rotate under load. The insert is typically made of a high wear plastic material that minimizes friction.

The condyle surface of femoral component 104 contacts a major surface of device 100. The major surface of device 100 approximates a surface of the insert. Tibial prosthetic component 106 can include a cavity or tray on the major surface that receives and retains an insert dock 202 and a sensing module 200 during a measurement process. Tibial prosthetic component 106 and device 100 have a combined thickness that represents a combined thickness of tibial prosthetic component 106 and a final (or chronic) insert of the knee joint.

In one embodiment, two devices 100 are fitted into two separate cavities, the cavities are within a trial insert (that may also be referred to as the tibial insert, rather than the tibial component itself) that is held in position by tibial component 106. One or two devices 100 may be inserted between femoral prosthetic component 104 and tibial prosthetic component 106. Each sensor is independent and each measures a respective condyle of femur 102. Separate sensors also accommodate a situation where a single condyle is repaired and only a single sensor is used. Alternatively, the electronics can be shared between two sensors to lower cost and complexity of the system. The shared electronics can multiplex between each sensor module to take measurements when appropriate.

Measurements taken by device 100 aid the surgeon in modifying the absolute loading on each condyle and the balance between condyles. Although shown for a knee implant, device 100 can be used to measure other orthopedic joints such as the spine, hip, shoulder, elbow, ankle, wrist, interphalangeal joint, metatarsophalangeal joint, metacarpophalangeal joints, and others. Alternatively, device 100 can also be adapted to orthopedic tools to provide measurements.

The prosthesis incorporating device 100 emulates the function of a natural knee joint. Device 100 can measure loads or other parameters at various points throughout the range of motion. Data from device 100 is transmitted to a receiving station 110 via wired or wireless communications. In a first embodiment, device 100 is a disposable system. Device 100 can be disposed of after using the load sensing insert device 100 to optimally fit the joint implant. Device 100 is a low cost disposable system that reduces capital costs, operating costs, facilitates rapid adoption of quantitative measurement, and initiates evidentiary based orthopedic medicine. In a second embodiment, a methodology can be put in place to clean and sterilize device 100 for reuse. In a third embodiment, device 100 can be incorporated in a tool instead of being a component of the replacement joint. The tool can be disposable or be cleaned and sterilized for reuse. In a fourth embodiment, device 100 can be a permanent component of the replacement joint. Device 100 can be used to provide both short term and long term post-operative data on the implanted joint. In a fifth embodiment, device 100 can be coupled to the muscular-skeletal system. In all of the embodiments, receiving station 110 can include data processing, storage, or display, or combination thereof and provide real time graphical representation of the level and distribution of the load. Receiving station 110 can record and provide accounting information of device 100 to an appropriate authority.

In an intra-operative example, device 100 can measure forces (Fx, Fy, and Fz) with corresponding locations and torques (e.g. Tx, Ty, and Tz) on the femoral prosthetic component 104 and the tibial prosthetic component 106. The measured force and torque data is transmitted to receiving station 110 to provide real-time visualization for assisting the surgeon in identifying any adjustments needed to achieve optimal joint pressure and balancing. The data has substantial value in determining ranges of load and alignment tolerances required to minimize rework and maximize patient function and longevity of the joint.

As mentioned previously, device 100 can be used for other joint surgeries; it is not limited to knee replacement implant or implants. Moreover, device 100 is not limited to trial measurements. Device 100 can be incorporated into the final joint system to provide data post-operatively to determine if the implanted joint is functioning correctly. Early determination of a problem using device 100 can reduce catastrophic failure of the joint by bringing awareness to a problem that the patient cannot detect. The problem can often be rectified with a minimal invasive procedure at lower cost and stress to the patient. Similarly, longer term monitoring of the joint can determine wear or misalignment that if detected early can be adjusted for optimal life or replacement of a wear surface with minimal surgery thereby extending the life of the implant. In general, device 100 can be shaped such that it can be placed or engaged or affixed to or within load bearing surfaces used in many orthopedic applications (or used in any orthopedic application) related to the musculoskeletal system, joints, and tools associated therewith. Device 100 can provide information on a combination of one or more performance parameters of interest such as wear, stress, kinematics, kinetics, fixation strength, ligament balance, anatomical fit and balance.

Figure 2:
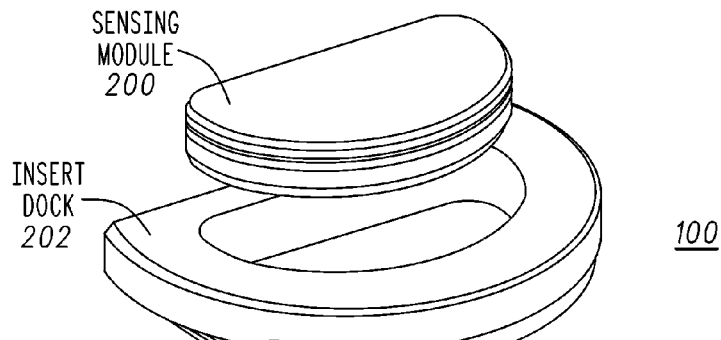
FIG. 2 is a perspective view of the medical device in accordance with one embodiment.

FIG. 2 is a perspective view of the medical device in accordance with one embodiment. As illustrated, the load sensing insert device 100 can include a sensing module 200 and an insert 202. The sensing Module 200 can securely fit within the insert dock 202. The insert dock 202 can securely attach or slide onto the tibial prosthetic component 106 (see FIG. 1). The prosthetic components of FIG. 2 can be manually coupled prior to surgical placement or during the surgery. The sensing module 200 in other embodiments (without the insert dock 202) can affix directly to load bearing surfaces exposed to forces, for example, forces applied upon a load bearing component during flexion of the joint. Although illustrated as separate, in yet another embodiment, the sensing module 200 and insert dock 202 can be combined together as an integrated sensing module.

The sensing module 200 is an encapsulating enclosure with a unitary main body and load bearing contact surfaces that can be, but are not limited to, dissimilar materials, combined to form a hermetic module or device. The components of the encapsulating enclosure may also consist of, but are not limited to, bio-compatible materials. For medical applications, the encapsulating enclosure may be required to be hermetic. The encapsulating enclosure can comprise biocompatible materials, for example, but not limited to, polycarbonate, steel, silicon, neoprene, and similar materials.

As will be discussed ahead, electronic assemblage within the sensing module 200 integrates a power supply, sensing elements, ultrasound resonator or resonators or transducer or transducers and ultrasound waveguide waveguides, biasing spring or springs or other form of elastic members, an accelerometer, antennas and electronic circuitry that processes measurement data as well as controls all operations of ultrasound generation, propagation, and detection and wireless communications. The electronics assemblage also supports testability and calibration features that assure the quality, accuracy, and reliability of the completed wireless sensing module or device. A temporary bi-directional interconnect assures a high level of electrical observability and controllability of the electronics. The test interconnect also provides a high level of electrical observability of the sensing sub-system, including the transducers, waveguides, and mechanical spring or elastic assembly. Carriers or fixtures emulate the final enclosure of the completed wireless sensing module or device during manufacturing processing thus enabling capture of accurate calibration data for the calibrated parameters of the finished wireless sensing module or device. These calibration parameters are stored within the on-board memory integrated into the electronics assemblage.

Figure 3:
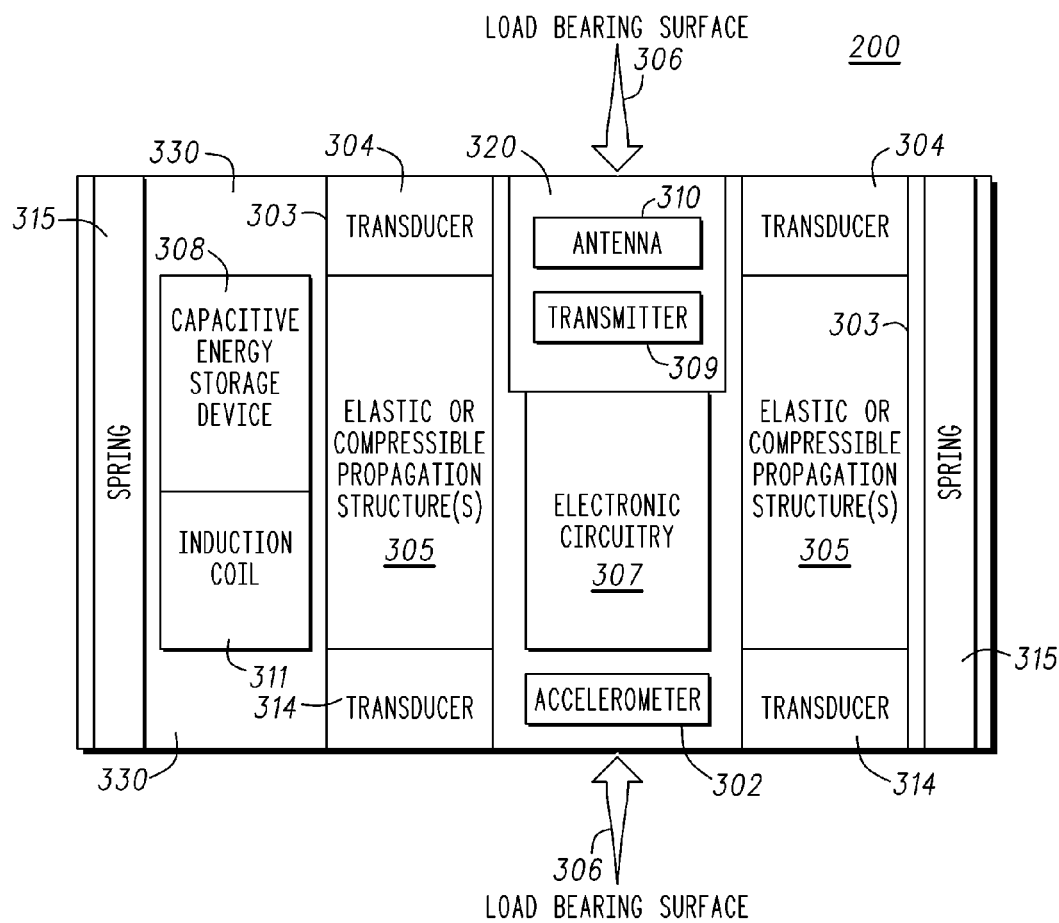
FIG. 3 is a block model diagram of a sensing module in accordance with one embodiment.

FIG. 3 is an exemplary block diagram of the components of a sensing module. It should be noted that the sensing module could comprise more or less than the number of components shown. As illustrated, the sensing module includes one or more sensing assemblages 303, a transceiver 320, an energy storage 330, electronic circuitry 307, one or more mechanical supports 315 (e.g., springs), and an accelerometer 302. In the non-limiting example, an applied compressive force can be measured by the sensing module.

The sensing assemblage 303 can be positioned, engaged, attached, or affixed to the contact surfaces 306. Mechanical supports 315 serve to provide proper balancing of contact surfaces 306. In at least one exemplary embodiment, contact surfaces 306 are load-bearing surfaces. In general, the propagation structure 305 is subject to the parameter being measured. Surfaces 306 can move and tilt with changes in applied load; actions which can be transferred to the sensing assemblages 303 and measured by the electronic circuitry 307. The electronic circuitry 307 measures physical changes in the sensing assemblage 303 to determine parameters of interest, for example a level, distribution and direction of forces acting on the contact surfaces 306. In general, the sensing module is powered by the energy storage 330.

As one example, the sensing assemblage 303 can comprise an elastic or compressible propagation structure 305 between a transducer 304 and a transducer 314. In the current example, transducer 304 can be an ultrasound (or ultrasonic) resonator, and the elastic or compressible propagation structure 305 can be an ultrasound (or ultrasonic) waveguide (or waveguides). The electronic circuitry 307 is electrically coupled to the sensing assemblages 303 and translates changes in the length (or compression or extension) of the sensing assemblages 303 to parameters of interest, such as force. It measures a change in the length of the propagation structure 305 (e.g., waveguide) responsive to an applied force and converts this change into electrical signals which can be transmitted via the transceiver 320 to convey a level and a direction of the applied force. In other arrangements herein contemplated, the sensing assemblage 303 may require only a single transducer. In yet other arrangements, the sensing assemblage 303 can include piezoelectric, capacitive, optical or temperature sensors or transducers to measure the compression or displacement. It is not limited to ultrasonic transducers and waveguides.

The accelerometer 302 can measure acceleration and static gravitational pull. Accelerometer 302 can be single-axis and multi-axis accelerometer structures that detect magnitude and direction of the acceleration as a vector quantity. Accelerometer 302 can also be used to sense orientation, vibration, impact and shock. The electronic circuitry 307 in conjunction with the accelerometer 302 and sensing assemblies 303 can measure parameters of interest (e.g., distributions of load, force, pressure, displacement, movement, rotation, torque and acceleration) relative to orientations of the sensing module with respect to a reference point. In such an arrangement, spatial distributions of the measured parameters relative to a chosen frame of reference can be computed and presented for real-time display.

The transceiver 320 comprises a transmitter 309 and an antenna 310 to permit wireless operation and telemetry functions. In various embodiments, the antenna 310 can be configured by design as an integrated loop antenna. As will be explained ahead, the integrated loop antenna is configured at various layers and locations on the electronic substrate with electrical components and by way of electronic control circuitry to conduct efficiently at low power levels. Once initiated the transceiver 320 can broadcast the parameters of interest in real-time. The telemetry data can be received and decoded with various receivers, or with a custom receiver. The wireless operation can eliminate distortion of, or limitations on, measurements caused by the potential for physical interference by, or limitations imposed by, wiring and cables connecting the sensing module with a power source or with associated data collection, storage, display equipment, and data processing equipment.

The transceiver 320 receives power from the energy storage 330 and can operate at low power over various radio frequencies by way of efficient power management schemes, for example, incorporated within the electronic circuitry 307. As one example, the transceiver 320 can transmit data at selected frequencies in a chosen mode of emission by way of the antenna 310. The selected frequencies can include, but are not limited to, ISM bands recognized in International Telecommunication Union regions 1, 2 and 3. A chosen mode of emission can be, but is not limited to, Gaussian Frequency Shift Keying, (GFSK), Amplitude Shift Keying (ASK), Phase Shift Keying (PSK), Minimum Shift Keying (MSK), Frequency Modulation (FM), Amplitude Modulation (AM), or other versions of frequency or amplitude modulation (e.g., binary, coherent, quadrature, etc.).

The antenna 310 can be integrated with components of the sensing module to provide the radio frequency transmission. The substrate for the antenna 310 and electrical connections with the electronic circuitry 307 can further include a matching network. This level of integration of the antenna and electronics enables reductions in the size and cost of wireless equipment. Potential applications may include, but are not limited to any type of short-range handheld, wearable, or other portable communication equipment where compact antennas are commonly used. This includes disposable modules or devices as well as reusable modules or devices and modules or devices for long-term use.

The energy storage 330 provides power to electronic components of the sensing module. It can be charged by wired energy transfer, short-distance wireless energy transfer or a combination thereof. External power sources can include, but are not limited to, a battery or batteries, an alternating current power supply, a radio frequency receiver, an electromagnetic induction coil, a photoelectric cell or cells, a thermocouple or thermocouples, or an ultrasound transducer or transducers. By way of the energy storage 330, the sensing module can be operated with a single charge until the internal energy is drained. It can be recharged periodically to enable continuous operation. The energy storage 330 can utilize common power management technologies such as replaceable batteries, supply regulation technologies, and charging system technologies for supplying energy to the components of the sensing module to facilitate wireless applications.

The energy storage 330 minimizes additional sources of energy radiation required to power the sensing module during measurement operations. In one embodiment, as illustrated, the energy storage 330 can include a capacitive energy storage device 308 and an induction coil 311. External source of charging power can be coupled wirelessly to the capacitive energy storage device 308 through the electromagnetic induction coil or coils 311 by way of inductive charging. The charging operation can be controlled by power management systems designed into, or with, the electronic circuitry 307. As one example, during operation of electronic circuitry 307, power can be transferred from capacitive energy storage device 308 by way of efficient step-up and step-down voltage conversion circuitry. This conserves operating power of circuit blocks at a minimum voltage level to support the required level of performance.

In one configuration, the energy storage 330 can further serve to communicate downlink data to the transceiver 320 during a recharging operation. For instance, downlink control data can be modulated onto the energy source signal and thereafter demodulated from the induction coil 311 by way of electronic control circuitry 307. This can serve as a more efficient way for receiving downlink data instead of configuring the transceiver 320 for both uplink and downlink operation. As one example, downlink data can include updated control parameters that the sensing module uses when making a measurement, such as external positional information, or for recalibration purposes, such as spring biasing. It can also be used to download a serial number or other identification data.

The electronic circuitry 307 manages and controls various operations of the components of the sensing module, such as sensing, power management, telemetry, and acceleration sensing. It can include analog circuits, digital circuits, integrated circuits, discrete components, or any combination thereof. In one arrangement, it can be partitioned among integrated circuits and discrete components to minimize power consumption without compromising performance. Partitioning functions between digital and analog circuit enhances design flexibility and facilitates minimizing power consumption without sacrificing functionality or performance. Accordingly, the electronic circuitry 307 can comprise one or more Application Specific Integrated Circuit (ASIC) chips, for example, specific to a core signal processing algorithm.

In another arrangement, the electronic circuitry can comprise a controller such as a programmable processor, a Digital Signal Processor (DSP), a microcontroller, or a microprocessor, with associated storage memory and logic. The controller can utilize computing technologies with associated storage memory such a Flash, ROM, RAM, SRAM, DRAM or other like technologies for controlling operations of the aforementioned components of the sensing module. In one arrangement, the storage memory may store one or more sets of instructions (e.g., software) embodying any one or more of the methodologies or functions described herein. The instructions may also reside, completely or at least partially, within other memory, and/or a processor during execution thereof by another processor or computer system.

Figure 4:
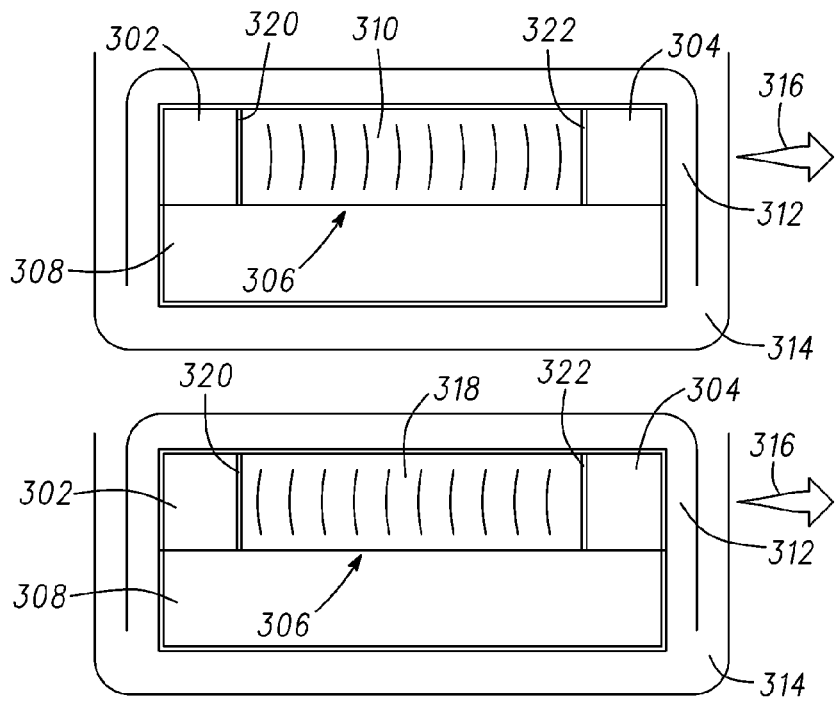
FIG. 4 is an exemplary assemblage that illustrates propagation of ultrasound waves within the waveguide in the bi-directional mode of operation of this assemblage in accordance with one embodiment.

FIG. 4 is an exemplary assemblage 300 that illustrates propagation of ultrasound waves 310 within the waveguide 306 in the bi-directional mode of operation of this assemblage. In this mode, the selection of the roles of the two individual ultrasound resonators (302, 304) or transducers affixed to interfacing material 320 and 322, if required, are periodically reversed. In the bi-directional mode the transit time of ultrasound waves propagating in either direction within the waveguide 306 can be measured. This can enable adjustment for Doppler effects in applications where the sensing module 308 is operating while in motion 316. Furthermore, this mode of operation helps assure accurate measurement of the applied load, force, pressure, or displacement by capturing data for computing adjustments to offset this external motion 316. An advantage is provided in situations wherein the body, instrument, appliance, vehicle, equipment, or other physical system 314, is itself operating or moving during sensing of load, pressure, or displacement. Similarly, the capability can also correct in situation where the body, instrument, appliance, vehicle, equipment, or other physical system, is causing the portion 312 of the body, instrument, appliance, vehicle, equipment, or other physical system being measured to be in motion 316 during sensing of load, force, pressure, or displacement. Other adjustments to the measurement for physical changes to system 314 are contemplated and can be compensated for in a similar fashion. For example, temperature of system 314 can be measured and a lookup table or equation having a relationship of temperature versus transit time can be used to normalize measurements. Differential measurement techniques can also be used to cancel many types of common factors as is known in the art.

The use of waveguide 306 enables the construction of low cost sensing modules and devices over a wide range of sizes, including highly compact sensing modules, disposable modules for bio-medical applications, and devices, using standard components and manufacturing processes. The flexibility to construct sensing modules and devices with very high levels of measurement accuracy, repeatability, and resolution that can scale over a wide range of sizes enables sensing modules and devices to the tailored to fit and collect data on the physical parameter or parameters of interest for a wide range of medical and non-medical applications.

Referring back to FIG. 1, although not explicitly illustrated, it should be noted that the load insert sensing device 100 and associated internal components move in accordance with motion of the femur 108 as shown. The bi-directional operating mode of the waveguide mitigates the Doppler effects resulting from the motion. As previously indicated, incorporating data from the accelerometer 121 with data from the other components of the sensing module 200 helps assure accurate measurement of the applied load, force, pressure, displacement, density, localized temperature, or viscosity by enabling computation of adjustments to offset this external motion.

For example, sensing modules or devices may be placed on or within, or attached or affixed to or within, a wide range of physical systems including, but not limited to instruments, appliances, vehicles, equipments, or other physical systems as well as animal and human bodies, for sensing the parameter or parameters of interest in real time without disturbing the operation of the body, instrument, appliance, vehicle, equipment, or physical system.

In addition to non-medical applications, examples of a wide range of potential medical applications may include, but are not limited to, implantable devices, modules within implantable devices, modules or devices within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment. Many physiological parameters within animal or human bodies may be measured including, but not limited to, loading within individual joints, bone density, movement, various parameters of interstitial fluids including, but not limited to, viscosity, pressure, and localized temperature with applications throughout the vascular, lymph, respiratory, and digestive systems, as well as within or affecting muscles, bones, joints, and soft tissue areas. For example, orthopedic applications may include, but are not limited to, load bearing prosthetic components, or provisional or trial prosthetic components for, but not limited to, surgical procedures for knees, hips, shoulders, elbows, wrists, ankles, and spines; any other orthopedic or musculoskeletal implant, or any combination of these.

Figure 5:
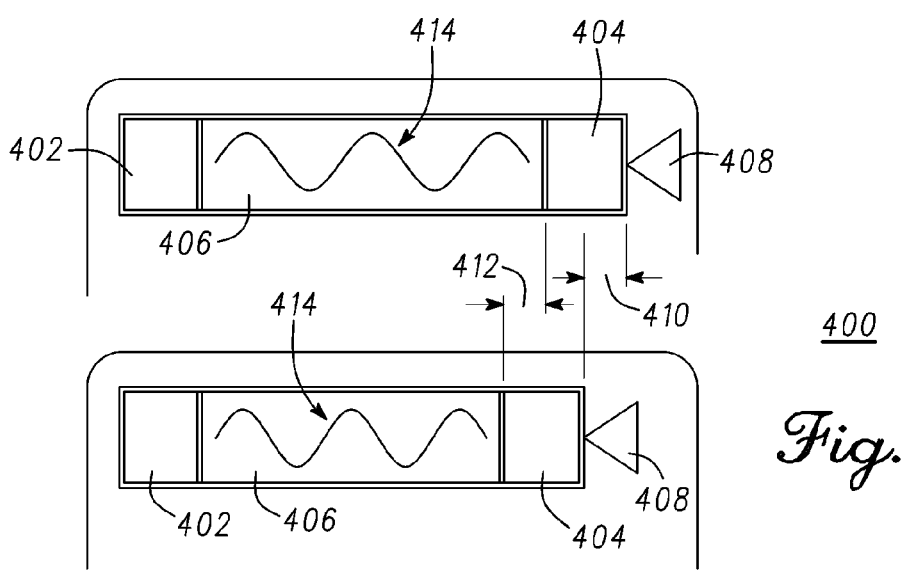
FIG. 5 is an exemplary cross-sectional view of an ultrasound waveguide to illustrate changes in the propagation of ultrasound waves with changes in the length of the waveguide in accordance with one embodiment.

FIG. 5 is an exemplary cross-sectional view of a sensor element 400 to illustrate changes in the propagation of ultrasound waves 414 with changes in the length of a waveguide 406. In general, the measurement of a parameter is achieved by relating displacement to the parameter. In one embodiment, the displacement required over the entire measurement range is measured in microns. For example, an external force 408 compresses waveguide 406 thereby changing the length of waveguide 406. Sensing circuitry (not shown) measures propagation characteristics of ultrasonic signals in the waveguide 406 to determine the change in the length of the waveguide 406. These changes in length change in direct proportion to the parameters of interest thus enabling the conversion of changes in the parameter or parameters of interest into electrical signals.

As previously discussed, external forces applied to the sensing module 200 compress the waveguide(s) thereby changing the length of the waveguide(s). The sensing module 200 measures propagation characteristics of ultrasonic signals in the waveguide(s) to determine the change in the length of the waveguide(s). These changes in length change in direct proportion to the parameters of interest thus enabling the conversion of changes in the parameter or parameters of interest into load (or force) information.

As illustrated, external force 408 compresses waveguide 406 and pushes the transducers 402 and 404 closer to one another by a distance 410. This changes the length of waveguide 406 by distance 412 of the waveguide propagation path between transducers 402 and 404. Depending on the operating mode, the sensing circuitry measures the change in length of the waveguide 406 by analyzing characteristics of the propagation of ultrasound waves within the waveguide.

One interpretation of FIG. 5 illustrates waves emitting from transducer 402 at one end of waveguide 406 and propagating to transducer 404 at the other end of the waveguide 406. The interpretation includes the effect of movement of waveguide 406 and thus the velocity of waves propagating within waveguide 406 (without changing shape or width of individual waves) and therefore the transit time between transducers 402 and 404 at each end of the waveguide. The interpretation further includes the opposite effect on waves propagating in the opposite direction and is evaluated to estimate the velocity of the waveguide and remove it by averaging the transit time of waves propagating in both directions.

Changes in the parameter or parameters of interest are measured by measuring changes in the transit time of energy pulses or waves within the propagating medium. Closed loop measurement of changes in the parameter or parameters of interest is achieved by modulating the repetition rate of energy pulses or the frequency of energy waves as a function of the propagation characteristics of the elastic energy propagating structure.

In a continuous wave mode of operation, a phase detector (not shown) evaluates the frequency and changes in the frequency of resonant ultrasonic waves in the waveguide 406. As will be described below, positive feedback closed-loop circuit operation in continuous wave (CW) mode adjusts the frequency of ultrasonic waves 414 in the waveguide 406 to maintain a same number or integer number of periods of ultrasonic waves in the waveguide 406. The CW operation persists as long as the rate of change of the length of the waveguide is not so rapid that changes of more than a quarter wavelength occur before the frequency of the propagation tuned oscillator (PTO) can respond. This restriction exemplifies one advantageous difference between the performance of a PTO and a Phase Locked Loop (PLL). Assuming the transducers are producing ultrasonic waves, for example, at 2.4 MHz, the wavelength in air, assuming a velocity of 343 microns per microsecond, is about 143μ, although the wavelength within a waveguide may be longer than in unrestricted air.

In a pulse mode of operation, the phase detector measures a time of flight (TOF) between when an ultrasonic pulse is transmitted by transducer 402 and received at transducer 404. The time of flight determines the length of the waveguide propagating path, and accordingly reveals the change in length of the waveguide 406. In another arrangement, differential time of flight measurements (or phase differences) can be used to determine the change in length of the waveguide 406. A pulse consists of a pulse of one or more waves. The waves may have equal amplitude and frequency (square wave pulse) or they may have different amplitudes, for example, decaying amplitude (trapezoidal pulse) or some other complex waveform. The PTO is holding the phase of the leading edge of the pulses propagating through the waveguide constant. In pulse mode operation the PTO detects the leading edge of the first wave of each pulse with an edge-detect receiver rather than a zero-crossing receiver circuitry as used in CW mode.

It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light.

Figure 6:
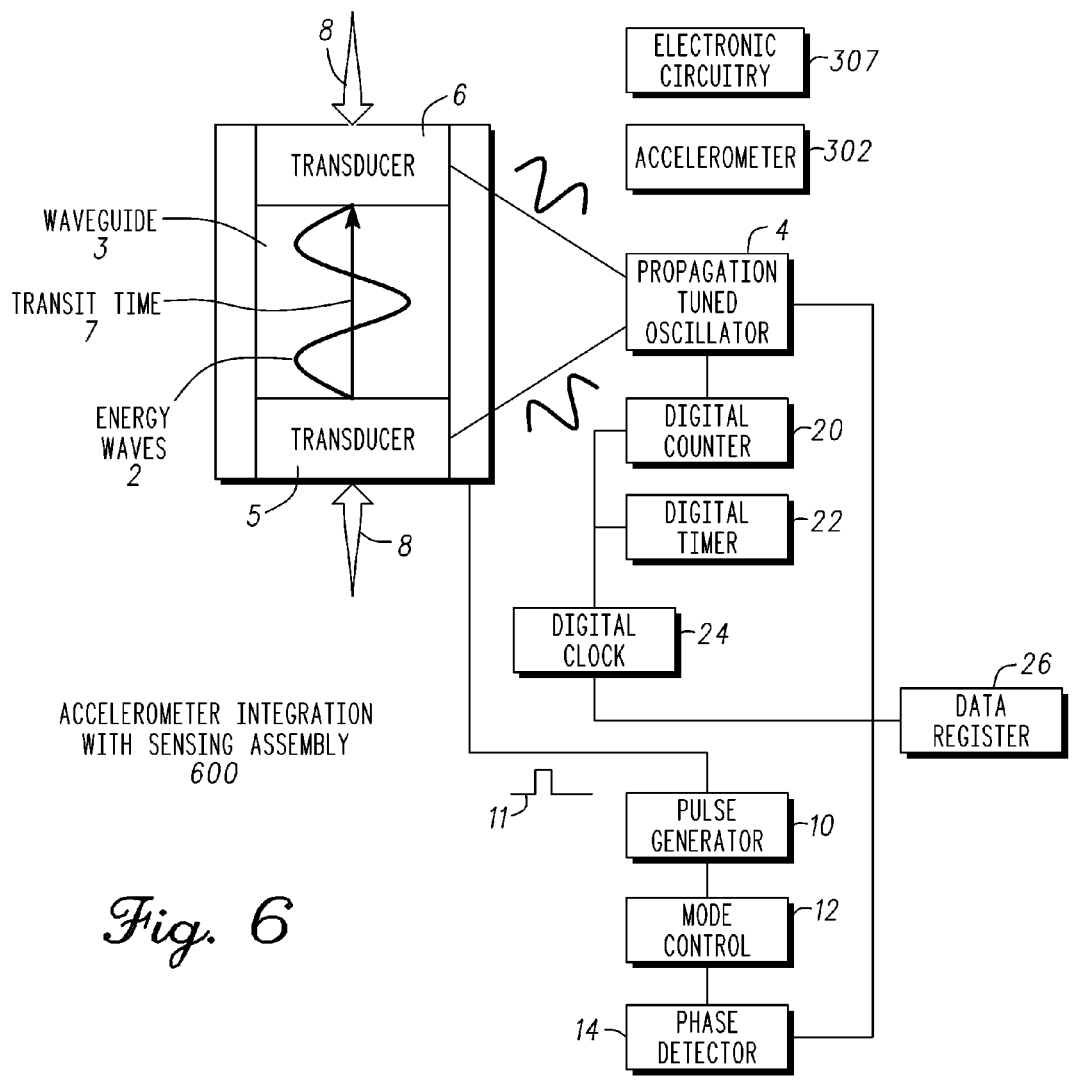
FIG. 6 is an exemplary block diagram of a propagation tuned oscillator (PTO) to maintain positive closed-loop feedback in accordance with an exemplary embodiment.

FIG. 6 is an exemplary block diagram 600 of a propagation tuned oscillator (PTO) 4 to maintain positive closed-loop feedback in accordance with an exemplary embodiment. The measurement system includes a sensing assemblage 1 and propagation tuned oscillator (PTO) 4 that detects energy waves 2 in one or more waveguides 3 of the sensing assemblage 1. In one embodiment, energy waves 2 are ultrasound waves. A pulse 11 is generated in response to the detection of energy waves 2 to initiate a propagation of a new energy wave in waveguide 3. It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light.

Recall that the load sensing insert device 100 when in motion measures forces on the sensing assemblies by evaluating propagation times of energy waves within the waveguides in conjunction with the accelerometer data. The propagation tuned oscillator (PTO) 4 measures a transit time of ultrasound waves 2 within the waveguide 3 in a closed-loop configuration. The digital counter 20 determines the physical change in the length of the waveguide. Referring to FIG. 3, the one or more accelerometers 302 determines the changes along x, y and z dimensions. The electronic circuitry 307 in view of the accelerometer data from accelerometer 302 and the physical changes in length of the sensing assemblage 1 determines the applied loading (or forces).

The sensing assemblage 1 comprises transducer 5, transducer 6, and a waveguide 3 (or energy propagating structure). In a non-limiting example, sensing assemblage 1 is affixed to load bearing or contacting surfaces 8. External forces applied to the contacting surfaces 8 compress the waveguide 3 and change the length of the waveguide 3. Under compression, transducers 5 and 6 will also be moved closer together. The change in distance affects the transit time 7 of energy waves 2 transmitted and received between transducers 5 and 6. The propagation tuned oscillator 4 in response to these physical changes will detect each energy wave sooner (e.g. shorter transit time) and initiate the propagation of new energy waves associated with the shorter transit time. As will be explained below, this is accomplished by way of PTO 4 in conjunction with the pulse generator 10, the mode control 12, and the phase detector 14.

Notably, changes in the waveguide 3 (energy propagating structure or structures) alter the propagation properties of the medium of propagation (e.g. transit time 7). The energy wave can be a continuous wave or a pulsed energy wave. A pulsed energy wave approach reduces power dissipation allowing for a temporary power source such as a battery or capacitor to power the system during the course of operation. In at least one exemplary embodiment, a continuous wave energy wave or a pulsed energy wave is provided by transducer 5 to a first surface of waveguide 3. Transducer 5 generates energy waves 2 that are coupled into waveguide 3. In a non-limiting example, transducer 5 is a piezo-electric device capable of transmitting and receiving acoustic signals in the ultrasonic frequency range.

Transducer 6 is coupled to a second surface of waveguide 3 to receive the propagated pulsed signal and generates a corresponding electrical signal. The electrical signal output by transducer 6 is coupled to phase detector 14. In general, phase detector 14 compares the timing of a selected point on the waveform of the detected energy wave with respect to the timing of the same point on the waveform of other propagated energy waves. In a first embodiment, phase detector 14 can be a zero-crossing receiver. In a second embodiment, phase detector 14 can be an edge-detect receiver. In the example where sensing assemblage 1 is compressed, the detection of the propagated energy waves 2 occurs earlier (due to the length/distance reduction of waveguide 3) than a signal prior to external forces being applied to contacting surfaces. Pulse generator 10 generates a new pulse in response to detection of the propagated energy waves 2 by phase detector 14. The new pulse is provided to transducer 5 to initiate a new energy wave sequence. Thus, each energy wave sequence is an individual event of energy wave propagation, energy wave detection, and energy wave emission that maintains energy waves 2 propagating in waveguide 3.

The transit time 7 of a propagated energy wave is the time it takes an energy wave to propagate from the first surface of waveguide 3 to the second surface. There is delay associated with each circuit described above. Typically, the total delay of the circuitry is significantly less than the propagation time of an energy wave through waveguide 3. In addition, under equilibrium conditions variations in circuit delay are minimal. Multiple pulse to pulse timings can be used to generate an average time period when change in external forces occur relatively slowly in relation to the pulsed signal propagation time such as in a physiologic or mechanical system. The digital counter 20 in conjunction with electronic components counts the number of propagated energy waves to determine a corresponding change in the length of the waveguide 3. These changes in length change in direct proportion to the external force thus enabling the conversion of changes in parameter or parameters of interest into electrical signals.

The block diagram 600 further includes counting and timing circuitry. More specifically, the timing, counting, and clock circuitry comprises a digital counter 20, a digital timer 22, a digital clock 24, and a data register 26. The digital clock 24 provides a clock signal to digital counter 20 and digital timer 22 during a measurement sequence. The digital counter 20 is coupled to the propagation tuned oscillator 4. Digital timer 22 is coupled to data register 26. Digital timer 20, digital timer, 22, digital clock 24 and data register 26 capture transit time 7 of energy waves 2 emitted by ultrasound resonator or transducer 5, propagated through waveguide 3, and detected by or ultrasound resonator or transducer 5 or 6 depending on the mode of the measurement of the physical parameters of interest applied to surfaces 8. The operation of the timing and counting circuitry is disclosed in more detail hereinbelow.

The measurement data can be analyzed to achieve accurate, repeatable, high precision and high resolution measurements. This method enables the setting of the level of precision or resolution of captured data to optimize trade-offs between measurement resolution versus frequency, including the bandwidth of the sensing and data processing operations, thus enabling a sensing module or device to operate at its optimal operating point without compromising resolution of the measurements. This is achieved by the accumulation of multiple cycles of excitation and transit time instead of averaging transit time of multiple individual excitation and transit cycles. The result is accurate, repeatable, high precision and high resolution measurements of parameters of interest in physical systems.

In at least one exemplary embodiment, propagation tuned oscillator 4 in conjunction with one or more sensing assemblages 1 are used to take measurements on a muscular-skeletal system. In a non-limiting example, sensing assemblage 1 is placed between a femoral prosthetic component and tibial prosthetic component to provide measured load information that aids in the installation of an artificial knee joint. Sensing assemblage 1 can also be a permanent component or a muscular-skeletal joint or artificial muscular-skeletal joint to monitor joint function. The measurements can be made in extension and in flexion. In the example, assemblage 1 is used to measure the condyle loading to determine if it falls within a predetermined range and location. Based on the measurement, the surgeon can select the thickness of the insert such that the measured loading and incidence with the final insert in place will fall within the predetermined range. Soft tissue tensioning can be used by a surgeon to further optimize the force or pressure. Similarly, two assemblages 1 can be used to measure both condyles simultaneously or multiplexed. The difference in loading (e.g. balance) between condyles can be measured. Soft tissue tensioning can be used to reduce the force on the condyle having the higher measured loading to reduce the measured pressure difference between condyles.

One method of operation holds the number of energy waves propagating through waveguide 3 as a constant integer number. A time period of an energy wave corresponds to energy wave periodicity. A stable time period is one in which the time period changes very little over a number of energy waves. This occurs when conditions that affect sensing assemblage 1 stay consistent or constant. Holding the number of energy waves propagating through waveguide 3 to an integer number is a constraint that forces a change in the time between pulses when the length of waveguide 3 changes. The resulting change in time period of each energy wave corresponds to a change in aggregate energy wave time period that is captured using digital counter 20 as a measurement of changes in external forces or conditions applied to contacting surfaces 8.

A further method of operation according to one embodiment is described hereinbelow for energy waves 2 propagating from transducer 5 and received by transducer 6. In at least one exemplary embodiment, energy waves 2 is an ultrasonic energy wave. Transducers 5 and 6 are piezo-electric resonator transducers. Although not described, wave propagation can occur in the opposite direction being initiated by transducer 6 and received by transducer 5. Furthermore, detecting ultrasound resonator transducer 6 can be a separate ultrasound resonator as shown or transducer 5 can be used solely depending on the selected mode of propagation (e.g. reflective sensing). Changes in external forces or conditions applied to contacting surfaces 8 affect the propagation characteristics of waveguide 3 and alter transit time 7. As mentioned previously, propagation tuned oscillator 4 holds constant an integer number of energy waves 2 propagating through waveguide 3 (e.g. an integer number of pulsed energy wave time periods) thereby controlling the repetition rate. As noted above, once PTO 4 stabilizes, the digital counter 20 digitizes the repetition rate of pulsed energy waves, for example, by way of edge-detection, as will be explained hereinbelow in more detail.

In an alternate embodiment, the repetition rate of pulsed energy waves 2 emitted by transducer 5 can be controlled by pulse generator 10. The operation remains similar where the parameter to be measured corresponds to the measurement of the transit time 7 of pulsed energy waves 2 within waveguide 3. It should be noted that an individual ultrasonic pulse can comprise one or more energy waves with a damping wave shape. The energy wave shape is determined by the electrical and mechanical parameters of pulse generator 10, interface material or materials, where required, and ultrasound resonator or transducer 5. The frequency of the energy waves within individual pulses is determined by the response of the emitting ultrasound resonator 4 to excitation by an electrical pulse 11. The mode of the propagation of the pulsed energy waves 2 through waveguide 3 is controlled by mode control circuitry 12 (e.g., reflectance or uni-directional). The detecting ultrasound resonator or transducer may either be a separate ultrasound resonator or transducer 6 or the emitting resonator or transducer 5 depending on the selected mode of propagation (reflectance or unidirectional).

In general, accurate measurement of physical parameters is achieved at an equilibrium point having the property that an integer number of pulses are propagating through the energy propagating structure at any point in time. Measurement of changes in the "time-of-flight" or transit time of ultrasound energy waves within a waveguide of known length can be achieved by modulating the repetition rate of the ultrasound energy waves as a function of changes in distance or velocity through the medium of propagation, or a combination of changes in distance and velocity, caused by changes in the parameter or parameters of interest.

It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light. Furthermore, the velocity of ultrasound waves within a medium may be higher than in air. With the present dimensions of the initial embodiment of a propagation tuned oscillator the waveguide is approximately three wavelengths long at the frequency of operation.

Measurement by propagation tuned oscillator 4 and sensing assemblage 1 enables high sensitivity and high signal-to-noise ratio. The time-based measurements are largely insensitive to most sources of error that may influence voltage or current driven sensing methods and devices. The resulting changes in the transit time of operation correspond to frequency, which can be measured rapidly, and with high resolution. This achieves the required measurement accuracy and precision thus capturing changes in the physical parameters of interest and enabling analysis of their dynamic and static behavior.

These measurements may be implemented with an integrated wireless sensing module or device having an encapsulating structure that supports sensors and load bearing or contacting surfaces and an electronic assemblage that integrates a power supply, sensing elements, energy transducer or transducers and elastic energy propagating structure or structures, biasing spring or springs or other form of elastic members, an accelerometer, antennas and electronic circuitry that processes measurement data as well as controls all operations of ultrasound generation, propagation, and detection and wireless communications. The electronics assemblage also supports testability and calibration features that assure the quality, accuracy, and reliability of the completed wireless sensing module or device.

In general, measurement of the changes in the physical length of individual waveguides can be made in several modes. Each assemblage of one or two ultrasound resonators or transducers combined with a waveguide can be controlled to operate in six different modes. This includes two wave shape modes: continuous wave or pulsed waves, and three propagation modes: reflectance, unidirectional, and bi-directional propagation of the ultrasound wave. In all modes of operation the changes in transit time within the ultrasound waveguides change the operating frequency of the propagation tuned oscillator 4 or oscillators. These changes in the frequency of oscillation of the propagation tuned oscillator or oscillators can be measured rapidly and with high resolution. This achieves the required measurement accuracy and precision thus enabling the capture of changes in the physical parameters of interest and enabling analysis of the dynamic and static behavior of the physical system or body.

The level of accuracy and resolution achieved by the integration of energy transducers and an energy propagating structure or structures coupled with the electronic components of the propagation tuned oscillator enables the construction of, but is not limited to, compact ultra low power modules or devices for monitoring or measuring the parameters of interest. The flexibility to construct sensing modules or devices over a wide range of sizes enables sensing modules to be tailored to fit a wide range of applications such that the sensing module or device may be engaged with, or placed, attached, or affixed to, on, or within a body, instrument, appliance, vehicle, equipment, or other physical system and monitor or collect data on physical parameters of interest without disturbing the operation of the body, instrument, appliance, vehicle, equipment, or physical system.

Figure 7:
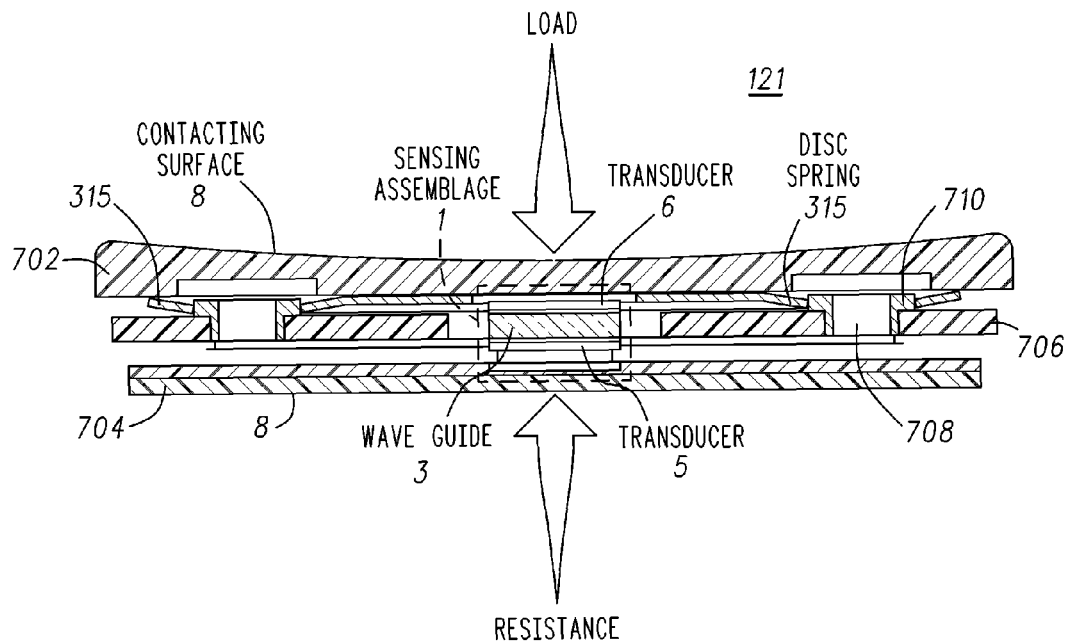
FIG. 7 is a simplified cross-sectional view of an embodiment of the load sensing platform in accordance with an exemplary embodiment.

FIG. 7 is a simplified cross-sectional view of an embodiment of the load sensing platform 121 in accordance with an exemplary embodiment. The load sensing platform 121 is placed, engaged, attached, or affixed to or within a physical system with a portion of the system contacting the load bearing or contacting surfaces of the load sensing platform. As disclosed in FIG. 1 the load sensing platform can be used intra-operatively to measure parameters of the muscular-skeletal system during joint replacement surgery. In the example, the load bearing platform 121 is placed in a joint of the muscular-skeletal system to measure force, pressure, or load and the location where the force, pressure, or load is applied. The lower load bearing surface 8 contacts the tibial component 106 of the artificial knee. The upper load bearing surface 8 contacts the femoral component 104 of the artificial knee. Not shown are the muscles, ligaments, and tendons of the muscular-skeletal system that apply a compressive force, pressure, or load on the surfaces 8 of the load sensing platform 121. The load sensing platform 121 has a form factor that allows integration in tools, equipment, and implants. The load sensing platform 121 is bio-compatible and can be placed in an implant or attached to the muscular-skeletal system to provide long term monitoring capability of natural structures or artificial components.

A compact sensing platform is miniaturized to be placed on or within a body, instrument, appliance, vehicle, equipment, or other physical system without disturbing the operation of the body, instrument, appliance, vehicle, equipment, or physical system. This facilitates contacting the sources of load, force, pressure, displacement, density, viscosity, or localized temperature to be measured. The non-limiting example of load sensing platform 121 can include circuitry disclosed in FIG. 3. Two or more springs or other means of elastic support 315 support the load bearing or contacting surfaces 8. One or more assemblages each comprised of one or two ultrasound resonators or transducers are coupled between load bearing surfaces 8.

As shown, a single sensing assemblage 1 is centrally located in load sensing platform 121. Sensing assemblage 1 is a stack comprising the upper transducer 6, the lower transducer 5, and the waveguide 3. In one embodiment, the waveguide 3 is cylindrical in shape having a first end and a second end. Transducers 5 and 6 respectively overlie the first and second ends of waveguide 3. An interface material can be used to attach and enhance acoustical coupling between a transducer and waveguide. The stack is positioned in contact with, attached, or coupled to the load bearing or contacting surfaces 8. Electrical interconnect such as a flex interconnect couples to terminals of transducers 5 and 6. The flex interconnect (not shown) electrically connects transducers 5 and 6 to electronic circuitry 307 of the sensing module 200.

The upper load bearing surface 8 is a surface of an upper substrate 702. An interior surface of the upper substrate 702 couples to transducer 6. Similarly, the lower load bearing surface 8 is a surface of a lower substrate 704. An interior surface of the lower substrate couples to the transducer 5. A load, force, or pressure applied across load bearing surfaces 8 can compress or lengthen waveguide 3. This arrangement facilitates translating changes in the parameter or parameters of interest into changes in the length or compression of the waveguide or waveguides 3 and converting these changes in the length or compression of the waveguide 3 or waveguides into electrical signals by way of transducers 5 or 6 thus enabling sensing assemblage 1 to sense changes in the physical parameters of interest with minimal disturbance to the operation of the external body, instrument, appliance, vehicle, equipment, or physical system. To achieve the required level of miniaturization, the length of the ultrasound waveguides 3 is on the order of 10 millimeters in length. The measurable resolution of compression or displacement of waveguide is on the order of sub-microns.

One or more springs 315 or other means of elastic support, support the load bearing or contacting surfaces 8. The one or more springs control a compression of load sensing platform 121. For example, waveguide 3 can comprise a polymer material suitable for energy wave propagation. In one embodiment, the polymer material changes dimension when a parameter to be measured is applied to waveguide 3. A relationship is known between the polymer material and a measured dimension. Changes in dimension are measured and the parameter calculated by way of the known relationship. The polymer material can exhibit mechanical hysteresis whereby the material in-elastically responds to changes in the applied parameter. In the example, the length of waveguide 3 responds to the force, pressure, or load applied across contacting surfaces 8. Moreover, the polymer material may not rebound in a timely fashion as the force, pressure or load changes. Springs 315 aid in the transition as waveguide 3 responds to different levels of compression. Springs 315 bring the load sensing platform 121 to an accurate and repeatable quiescent state or condition. Springs further prevent the cantilevering of load bearing surfaces 8 that can reduce an accuracy of measurement. Cantilevering becomes more prevalent as forces, pressures, and loads are applied towards the periphery of a contact area of load bearing surfaces 8.

In one embodiment, the springs 315 that support load bearing surfaces 8 are disc springs or a wave springs. Disc springs are capable of maintaining waveguide 3 at a precise length. The compression of the waveguide 3 is very accurate over the measurement range. The compression of the disc springs can be monotonic over the range of applied levels of force, pressure, or load. In one embodiment, the surfaces of the disc springs are polished to assure smooth compression with changes in force applied to contact surfaces 8. A further benefit of the disk springs is that they eliminate or minimize cantilevering of the load supporting substrate that can compromise the accuracy due to the inclination of load bearing surfaces 8. In the illustration, two springs 315 are shown that are located on the periphery of load sensing platform 121.

Although not shown, other springs 315 may reside in the load sensing platform 121 at other predetermined locations. Typically, the contact area where the parameter is applied to load bearing surfaces 8 is within an area bounded by springs 315.

In one embodiment, a substrate 706 is resides between upper substrate 702 and lower substrate 704. Sensing assemblage 1 couples through an opening in substrate 706 to couple to the interior surfaces of substrates 702 and 704 to measure a force, pressure, or load applied across load bearing surfaces 8. Substrates 704 and 706 are planar to one another separated by a predetermined spacing. Substrates 704 and 706 remain in the fixed relation to one another under loading.

Springs 315 are placed between an upper surface of substrate 706 and the interior surface of substrate 702. As disclosed in the example, springs 315 are disc springs. The disc springs are concave in shape. The disc spring is formed having a centrally located circular opening. The surface of springs 315 proximally located to the circular opening contacts the upper surface of substrate 706. The surface of springs 315 proximally located to the outer edge of springs 315 contacts the interior surface of substrate 702. A force applied across the load bearing surface 8 of load sensing platform 121 will compress springs 315 and waveguide 3. The amount of compression of waveguide 3 over a measurable range can be very small but will provide precision accuracy of the parameter. For example, waveguide 3 may be compressed less than a millimeter for a force measurement ranging from 5 to 100 lbs. In the example, the length of waveguide 3 is precisely measured using acoustic energy wave propagation. The measured length is then converted to the force, pressure, or load. The springs 315 support movement of the waveguide 3 upon a change in force, pressure, or loading. For example, springs 315 repeatably return the load sensing platform 121 to a precise quiescent state upon releasing an applied force. The characteristics of springs 315 are known over the measurement range of load sensing platform 121. The calculated measured value of the parameter can include compensation due to springs 315.

Spring 315 are in a fixed location in load sensing platform 121. The disc springs are located on the periphery of the load sensing platform 121. Spring posts 708 and spring retainers 710 are used to align and fix springs 315 in each predetermined location. Spring post 708 aligns substrate 702 to substrate 706. Spring post 708 and spring retainer 710 aligns to corresponding openings in substrate 706. In one embodiment, a cap of post 708 fits into a corresponding cavity of the interior surface of substrate 702. Spring retainer 710 is a sleeve that overlies post 708. Post 708 and spring retainer 710 couples through a corresponding opening in substrate 706. Spring retainer 710 has a lip that overlies and contacts the upper surface of substrate 706. The spring post 708 and spring retainer 710 couple through the opening in the disc spring. The edge of the opening rests against the edge of the lip of retainer 710 thereby retaining and holding spring 315 in the predetermined location. Spring 315 can move vertically allowing waveguide 3 to change length due to the parameter being applied to contact surfaces 8.

In one embodiment, load sensing platform 121 can locate a position where the parameter is applied on a load bearing surface. Locating the position can be achieved by using more than one sensing assemblages 1. In one embodiment, three sensing assemblages 1 couple to load bearing or contacting surface 8 at three predetermined locations. The parameter is measured by each sensing assemblages 1. The magnitudes of each measurement and the differences between measurements of the sensing assemblages 1 are compared. For example, the location of the applied parameter is closer to the sensing assemblage that generates the highest reading. Conversely, the location of the applied parameter will be furthest from the sensing assemblage that generates the lowest reading. The exact location can be determined by comparison of the measured values of each sensing assemblage in conjunction with knowledge of the predetermined locations where each assemblage contacts load bearing or contacting surface 8.

Figure 8:
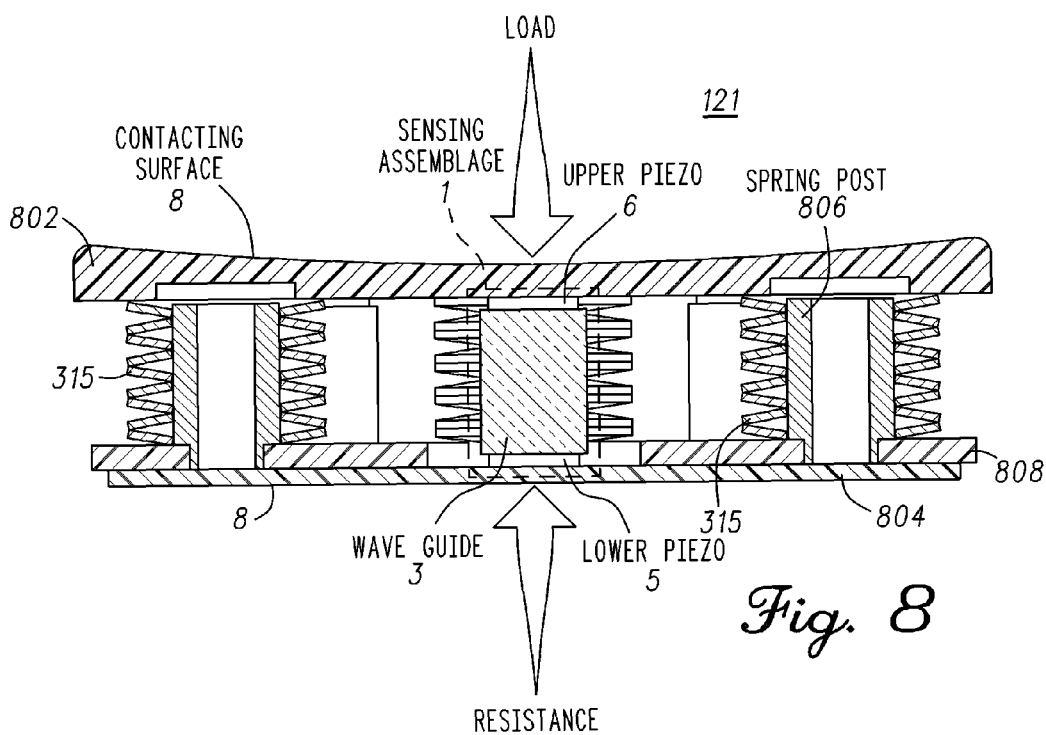
FIG. 8 is a simplified cross-sectional view illustrating a spring arrangement of the load sensing platform in accordance with an alternate embodiment.

FIG. 8 is a simplified cross-sectional view illustrating a spring arrangement of the load sensing platform 121 in accordance with one embodiment. The example assemblage includes a transducer 5, a waveguide 3, a transducer 6 and one or more springs 315 or individual member of other means of elastic support positioned in contact with or affixed to the load bearing or contacting surfaces 8. The assemblage illustrates the relationship of components comprising each assemblage to the load bearing or contacting surfaces and the reaction of these sensing components to external load, force, pressure, displacement, density, viscosity, or localized temperature.

In one embodiment, the length of ultrasound waveguide 3 is less than ten millimeters to facilitate a greater range of motion with respect to displacement. Individual applications may require a longer waveguide or shorter waveguides, other wavelengths of ultrasound, other waveguide materials, or the measurement of greater levels of load, force, or pressure, or greater movement by the contacting physical object, fluid, or gas pressing against the load bearing or contacting surfaces 8 of the load sensing platform 121. Two or more springs 315 or other means of elastic support couple to the load bearing or contacting surfaces 8. One or more assemblages 1 each comprised of one or more resonators or transducers (5 and 6) and an ultrasound waveguide 3 are positioned in contact with or attached or affixed to the load bearing or contacting surfaces 8. This arrangement facilitates translating changes in the parameter or parameters of interest into changes in the length or compression of the waveguide or waveguides 3 and converting these changes in the length or compression of the waveguide or waveguides 3 into electrical signals thus enabling the load sensing platform 121 to sense changes in the physical parameters of interest with minimal disturbance to the operation of an external body, instrument, appliance, vehicle, equipment, or physical system. Resolution of compression or displacement is on the order of sub-microns.

The load sensing platform 121 has a centrally located sensing assemblage 1. In one embodiment, sensing assemblage 1 is located within an open interior space of spring 315. The centrally located spring 315 provides elastic support to waveguide 3. There are also more than one spring 315 located around the periphery to further provide elastic support and to reduce cantilevering. In the example, springs 315 can be conventional coil springs or disc springs. As disclosed above, spring posts 806 and spring retainer 810 aid in alignment and maintaining springs 315 in a fixed location. Springs 315 overlie spring posts 806. Spring posts 806 are coupled to upper substrate 802. Spring posts 806 have a cap that fits in a cavity of an inner surface of substrate 802. Spring retainer 810 retains springs 315 positionally to lower substrate 804. In one embodiment, spring retainer 810 is a substrate that couples to the lower substrate 804. Spring retainer 810 has openings to receive/align spring posts 810 and allows transducer 5 to couple to lower substrate 804.

Exemplary level of control of the compression or displacement of ultrasound waveguide or waveguides with changes in load, force, pressure, displacement, density, or viscosity is achieved by positioning the spring or springs or other means of elastic support between the load bearing or contact surfaces to minimize any tendency of the load bearing or contact surface or surfaces to cantilever and thus compromise the accuracy of the inclination of the load bearing or contact surfaces whenever load, force, pressure, density, or displacement is applied to any point within the periphery of the load bearing or contact surface or surfaces. The lateral dimensions of each spring or individual member of other means of elastic support can be constrained by two factors. The size of the area of each individual spring or individual member of other means of elastic support at the point where it supports the load bearing or contact surface or surfaces is small enough to minimize any tendency for the load bearing or contact surface to cantilever and thus compromise the accuracy of the inclination of the load bearing or contact surfaces whenever load, force, pressure, density or displacement are applied to any point within the periphery of the load bearing or contact surface or surfaces. In embodiments that utilize a combination of springs, or other means of elastic support having multiple members, and waveguides, the length of each spring or each individual member of other means of elastic support is the same as the length of each ultrasound waveguide.

The resistance to compression for a given load, force, or pressure is strong enough to support the maximum load, force, or pressure without damage to the ultrasound resonators or transducers, the waveguides, or the springs or other means of elastic support, while achieving a linear displacement throughout the entire range of measurements of the applied load, force, or pressure. Also, the extent to which the ultrasound waveguides and springs or other means of elastic support may be compressed or extended without damage to the ultrasound resonators or transducers, waveguides, or the springs or other means of elastic support, must be selected to accommodate the maximum travel of external physical objects or surfaces contacting the load bearing or contact surface or surfaces. In embodiments wherein the load bearing or contacting surfaces are supported by the ultrasound waveguide or waveguides, the waveguides have these elastic properties. In embodiments wherein the load bearing or contacting surfaces are supported by separate spring, springs, or other elastic structure with these properties, the elasticity of the waveguides is such that all mechanical support for the load bearing or contacting surfaces is accomplished by the spring, springs, or other elastic structure.

The waveguide or waveguides are constructed of elastic materials that provide a suitable medium for propagating ultrasonic waves. Changes in compression or displacement of the waveguide or waveguides alter their physical length and are detectable by changes in the transit time of ultrasound waves propagating therein. The center or focal point (or locus or centroid) of the applied load, force, pressure, displacement, density, or viscosity on the load bearing or contacting surfaces may be determined by combining measurements taken with a combination of assemblages of ultrasound resonators or transducers and waveguides.

Measurement of the changes in the physical length of individual waveguides may be made in several modes. Each assemblage of one or two ultrasound resonators or transducers combined with a waveguide may be controlled to operate in six different modes. This includes two wave shape modes: continuous wave or pulsed waves, and three propagation modes: reflectance, unidirectional, and bi-directional propagation of the ultrasound wave.

The load bearing or contacting surfaces may be configured to interface with externally applied load, force, pressure, displacement, density, or viscosity in multiple configurations. The materials and shapes of the load bearing or contacting surfaces are determined by the parameter or parameters to be measured, the interface requirements of the sources of the load, force, pressure, and displacements, and the operating environment. The load bearing or contacting surfaces may be rigid with no measurable flexure at maximum load, pressure, displacement, density, or viscosity, or they may deform plastically without set or hysteresis regaining original shape rapidly enough to assure measurement of the transit times through the associated waveguide or waveguides are accurate and repeatable.

For applications wherein an embodiment of the invention is placed, engaged, attached, or affixed on or within a physical system having a member or members positioned in contact with or engaging or affixed to the load bearing or contacting surfaces, extension of the ultrasound waveguides may be detected as well as compression or displacement. The resulting change in the transit time of ultrasound waves propagating within the waveguides may be captured and processed in all the modes of operation of the assemblages of one or two ultrasound resonators or transducers and waveguides as previously described.

Figure 9:
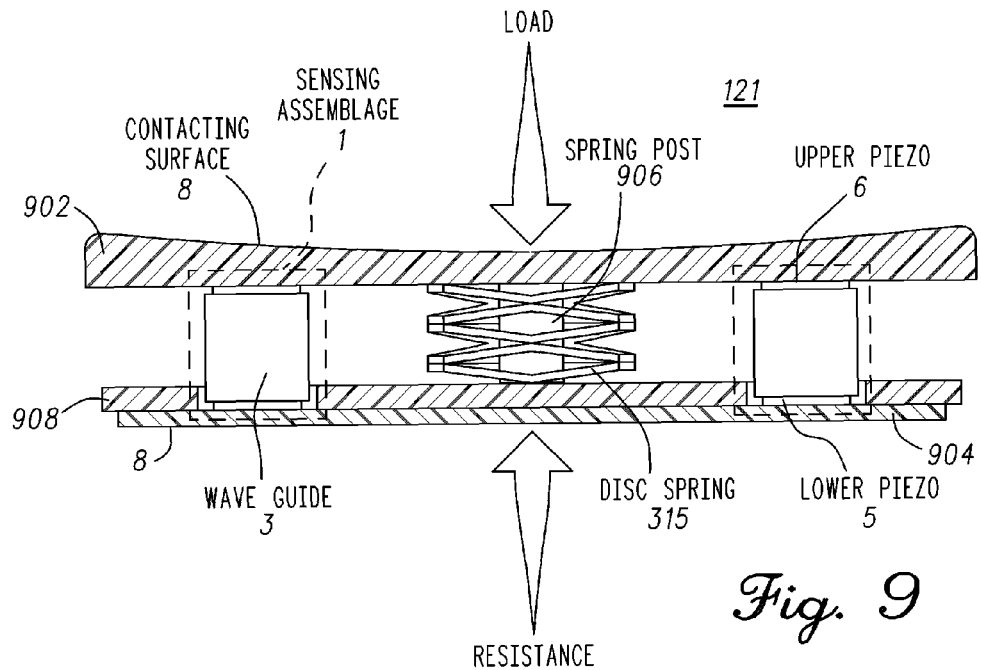
FIG. 9 is a simplified cross-sectional view illustrating a spring arrangement of the load sensing platform in accordance with an alternate embodiment.

FIG. 9 is a simplified cross-sectional view illustrating a spring arrangement of the load sensing platform 121 in accordance with an alternate embodiment. In one embodiment, a single spring supports the load bearing or contacting surfaces 8. The spring 315 contacts the interior surfaces of substrates 902 and 904. Spring 315 supports a large area of the interior surfaces of substrates 902. In the example, spring 315 can be a conventional coil springs, a disc spring, or other suitable spring. As disclosed above, spring post 906 and spring retainer 908 aid in alignment and to maintain spring 315 in a fixed location or position within the assembly. Spring 315 overlies spring post 906 that is coupled to upper substrate 902. Spring post 906 has a cap that fits in a cavity of an inner surface of substrate 902. Spring retainer 908 retains spring 315 positionally to lower substrate 904. In one embodiment, spring retainer 908 is a substrate that couples to the lower substrate 904. Spring retainer 908 has openings to receive/align spring post 906 and allows transducer 5 to couple to lower substrate 904.

More than one assemblage 1 is located on a perimeter of load sensing platform 121. Sensing assemblage 1 comprises a transducer 5, transducer 6, and an ultrasound waveguide 3. The transducer 5 and 6 is respectively coupled to a first location and a second location of waveguide 3. Transducers 5 and 6 are positioned in contact with, attached, or coupled to the interior surfaces of substrates 902 and 904. In particular, transducers 5 couple to the interior surface of substrate 904. Transducers 6 couple to the interior surface of substrate 902. A force applied across load bearing surfaces 8 will compress sensing assemblages 1. In an alternate embodiment, sensing assemblages 1 can comprise a single transducer, a reflecting surface, and waveguide 3. The reflecting assemblage embodiment can be used in all the embodiments disclosed herein. The single transducer and reflecting surface is respectively coupled to waveguide 3 at the first and second locations. The single transducer emits and detects energy waves. The reflecting surface reflects propagated energy waves back to the single transducer. The central spring embodiment has applications in cases where multiple springs or means of elastic support are not necessary or do not fit the required form factor for the load sensing platform.

Figure 10:
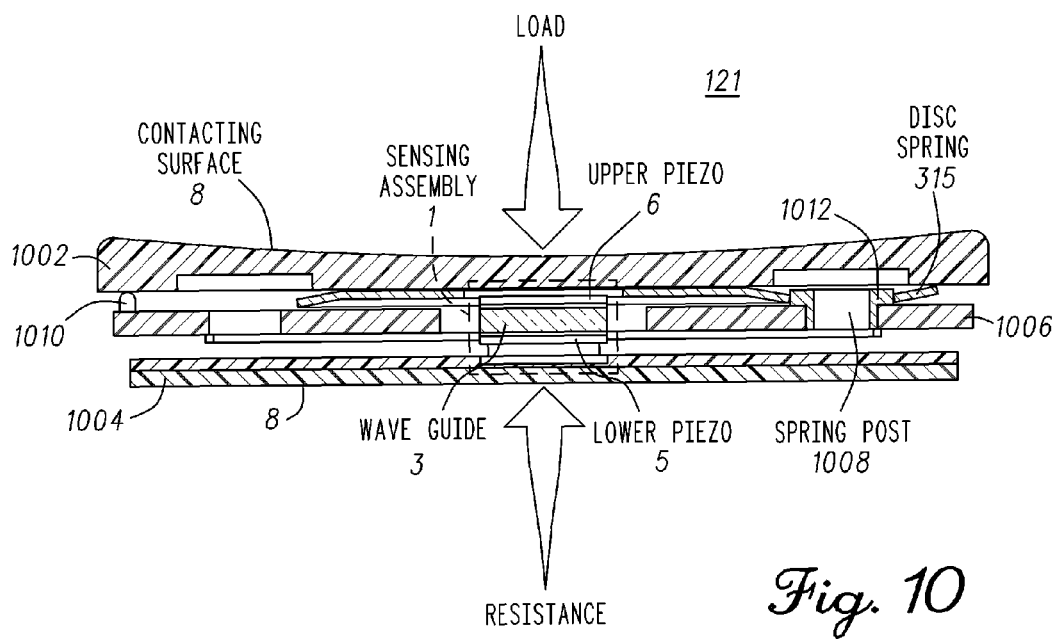
FIG. 10 is a simplified cross-sectional view illustrating a spring arrangement of the load sensing platform in accordance with an alternate embodiment.

FIG. 10 is a simplified cross-sectional view illustrating a spring arrangement of the load sensing platform 121 in accordance with an alternate embodiment. The embodiment places a spring 315 on one side of the periphery of the load sensing platform 121. The spring 315 or individual member of other means of elastic support supports the load bearing or contacting surfaces 8 that are constrained by a feature 1010. The feature 1010 can be a hinge, one or more stops, a combination of hinge and stops, or a fulcrum. In the embodiment, the sensing assemblage 1 is centrally located in load sensing platform 121. The sensing assemblage 1 comprises transducer 5, transducer 6, and waveguide 3. The sensing assemblage 1 is positioned to be in contact with, attached, or coupled to interior surfaces of substrates 1002 and 1004. A substrate 1006 is between substrates 1002 and 1004. The sensing assemblage 1, springs 315, spring post 1008, and spring retainer 1012 are connected similar to that described in FIG. 7 at the locations shown in FIG. 10. The use of feature 1010 may be applicable in cases where a single small spring or means of elastic support can be positioned to fit the required form factor for the load sensing platform 121.

Figure 11:
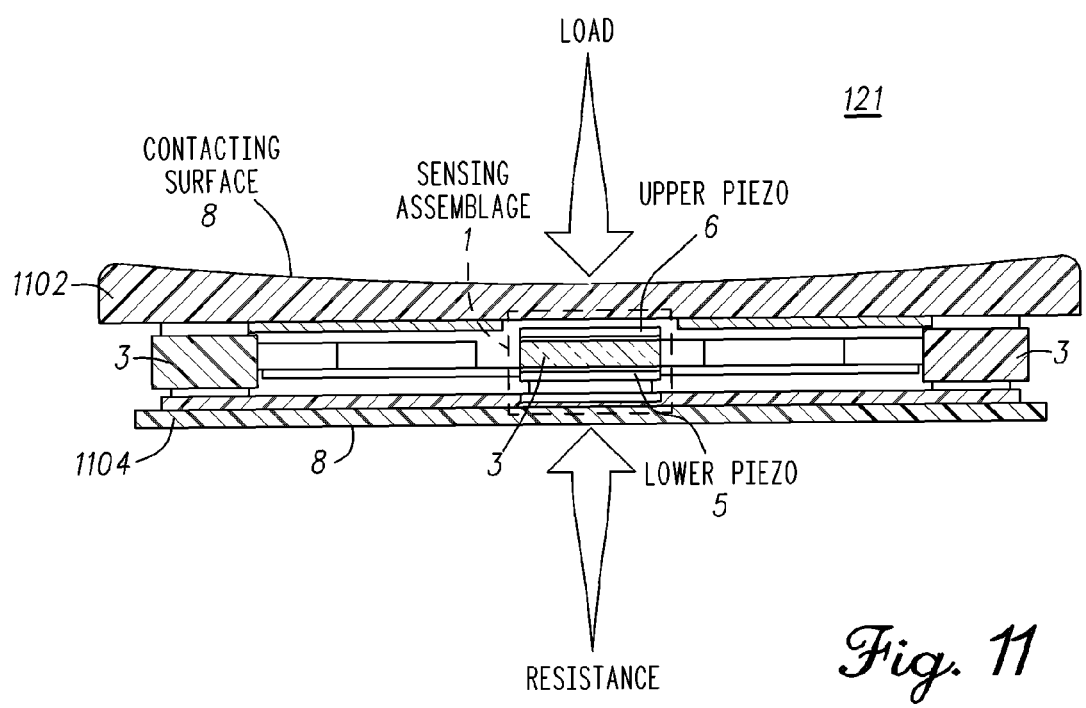
FIG. 11 is a simplified cross-sectional view illustrating a spring arrangement of the load sensing platform in accordance with an alternate embodiment.

FIG. 11 is a simplified cross-sectional view illustrating a spring arrangement of the load sensing platform 121 in accordance with an alternate embodiment. The embodiment comprises one or more compressible waveguides 3. The waveguides 3 are constructed of elastic material with a compression response to applied load, force, pressure, density, viscosity or displacement suitable to perform the function of a spring or springs or other means of elastic support. The sensing assemblage 1 is centrally located in load sensing platform 121. The sensing assemblage 1 comprises transducer 5, transducer 6, and waveguide 3. The sensing assemblage 1 is positioned to be in contact with, attached, or coupled to interior surfaces of substrates 1102 and 1104.

The resistance to compression of waveguide 3 for a given load, force, or pressure is sufficient to support the maximum load, force, or pressure applied to load bearing surfaces 8 without damage to the transducers 4 or 5. Sensing assemblage 1 achieves a linear displacement throughout the entire range of measurements of the applied load, force, or pressure. Waveguides 3 are placed on the periphery of load sensing platform 121 similar to the location of the disc springs of FIG. 7. The waveguides 3 on the periphery act as springs to respond to forces, pressures or loading on contact surfaces 8. The waveguides 3 repeatably bring the load sensing platform to a precise quiescent state when unloaded. Furthermore, the waveguides 3 is an elastic material that reduces cantilevering. The embodiment eliminates the requirement for a separate spring or springs or other means of elastic support. This is applicable in cases where separate springs or means of elastic support are not necessary or do not fit the required form factor for the load sensing platform.

Other configurations will be described briefly herein below for a load sensing platform. In a first brief embodiment, the load sensing platform comprises parallel load bearing or contacting surfaces, one or more ultrasound resonators or transducers, one or more waveguides, and one or more springs or other means of elastic support. The springs are positioned or affixed between two load bearing or contacting surfaces normal to the plane of the load bearing or contacting surfaces. This is applicable in cases where parallel load bearing or contacting surfaces 8 facilitate contacting the external sources of load, force, pressure, density, viscosity, or displacement to be measured with minimal disturbance to the operation of an external body, instrument, appliance, vehicle, equipment, or physical system.

In a second brief embodiment, the load sensing platform comprises two load bearing or contacting surfaces, one or more ultrasound resonators or transducers, one or more waveguides, and one or more springs or other means of elastic support. The load bearing or contact surfaces are positioned parallel to a line connecting the center points of the two load bearing or contacting surfaces. The contacting surfaces are not parallel in this embodiment. This is applicable in cases where nonparallel load bearing or contacting surfaces 8 facilitate contacting the external sources of load, force, pressure, density, viscosity, or displacement to be measured with minimal disturbance to the operation of the external body, instrument, appliance, vehicle, equipment, or physical system.

In a third brief embodiment, a load sensing platform comprises an instance of three or more load bearing or contacting surfaces, one or more ultrasound resonators or transducers, one or more waveguides, and one or more springs or other means of elastic support. The contacting surfaces are positioned parallel to lines connecting the center points of each pair of load bearing or contacting surfaces. This is applicable in cases where more than two load bearing or contacting surfaces facilitate contacting the external sources of load, force, pressure, density, viscosity, or displacement to be measured with minimal disturbance to the operation of the external body, instrument, appliance, vehicle, equipment, or physical system.

In a fourth brief embodiment, a load sensing platform comprises two curvilinear load bearing or contacting surfaces with complex shapes, one or more ultrasound resonators or transducers, one or more waveguides, and one or more springs or other means of elastic support. The contacting surfaces are positioned parallel to a line connecting the points on the two curvilinear load bearing or contacting surfaces as required to effectively interface with the external sources of load, force, pressure displacement, density, viscosity, or localized temperature. This can readily be extended to load bearing and contact surfaces having any form of complex shapes. This can also readily be extended to any combination of a complex shape or curvilinear load bearing or contacting surface and a plane load bearing or contacting surface or combinations of multiple plane, curvilinear, and complex shaped load bearing or contacting surfaces as required by individual applications. This may be applicable in cases where plane load bearing or contacting surfaces may not be adequate or preferred for contacting the external sources of load, force, pressure, displacement, density, viscosity, or localized temperature to be measured reliable with only minimal disturbance to the operation of the external body, instrument, appliance, vehicle, equipment, or physical system.

In general, the load sensing platform includes predetermined positions of springs or other means of elastic support to compressible waveguide sensors acting as the principal form of elastic support to reliably translate changes in the parameter or parameters of interest into changes in the length, compression, or displacement of the one or more waveguides. Control of the compression or displacement of the waveguide with changes in load, force, pressure, displacement, density, or viscosity is achieved by positioning the spring or springs or other means of elastic support between the load bearing or contact surfaces to minimize any tendency for the load bearing or contact surface or surfaces to cantilever. Cantilevering can compromise the accuracy of the inclination of the load bearing or contact surfaces whenever load, forces, pressure, density, viscosity, or displacement is applied to any point within the periphery of the load bearing or contact surface or surfaces. In embodiments disclosed herein that utilize a combination of springs or other means of elastic support and waveguides for measurement, the length of each spring is approximately the same as the length of each ultrasound waveguide.

Various benefits of the disclosed embodiments are disclosed hereinbelow. Switching of ultrasound transducers between receive and transmit modes can be performed to detect reflected waves without locking onto artifacts of the transmitted waves allowing a single transducer to be used with a waveguide. Accurate translation of pressure to compression is possible with various embodiments of the waveguides that have much lower resistance to pressure (more elastic and compressible) than springs. Placing three sensing assemblages at predetermined locations are an effective configuration for sensing amplitude and location of a parameter applied to the sensing platform. Typically, the parameter is applied within an area bounded by the three assemblages. Similarly, three springs can be used to support the three sensing assemblages. Polyethylene and urethane materials are suitable for ultrasound waveguides. The polymer materials do exhibit mechanical hysteresis and can take a compression set. The compression set results in the waveguide not returning quickly enough to the pre-stressed length to assure accurate and repeatable measurements. Springs or other means of elastic support are used to counter mechanical hysteresis. In particular, disk springs maintain precise length of ultrasound waveguides as well as accurate (monotonic) compression of waveguides over the range of applied levels of force. In one embodiment, the surface of the disk springs are polished during manufacturing to assure smooth compression with changes in force applied to the load bearing surfaces of the load sensing assembly. The disk springs can provide improved detection of level and position of force because they do not cantilever the load bearing surfaces as some other forms of springs would. Furthermore, disk springs do not deform in direct relationship with the strength and location of the applied force thereby providing an improved response of both the level and location.

Many physical parameters of interest within physical systems or bodies can be measured by evaluating changes in the characteristics of energy waves or pulses. As one example, changes in the transit time or shape of an energy wave or pulse propagating through a changing medium can be measured to determine the forces acting on the medium and causing the changes. The propagation velocity of the energy waves or pulses in the medium is affected by physical changes in of the medium. The physical parameter or parameters of interest can include, but are not limited to, measurement of load, force, pressure, displacement, density, viscosity, localized temperature. These parameters can be evaluated by measuring changes in the propagation time of energy pulses or waves relative to orientation, alignment, direction, or position as well as movement, rotation, or acceleration along an axis or combination of axes by wireless sensing modules or devices positioned on or within a body, instrument, appliance, vehicle, equipment, or other physical system.

The parameters can be measured with an integrated wireless sensing module or device comprising an encapsulating structure that supports sensors and load bearing or contacting surfaces, an electronic assemblage that integrates a power supply, sensing elements, ultrasound resonator or resonators or transducer or transducers and ultrasound waveguide or waveguides, biasing spring or springs or other form of elastic members, an accelerometer, antennas and electronic circuitry that processes measurement data as well as controls all operations of energy conversion, propagation, and detection and wireless communications. The wireless sensing module or device can be positioned on or within, or engaged with, or attached or affixed to or within, a wide range of physical systems including, but not limited to instruments, appliances, vehicles, equipments, or other physical systems as well as animal and human bodies, for sensing and communicating parameters of interest in real time.

In general, a parameter is applied to a load bearing surface of the load sensing platform. The parameter affects a medium such as a waveguide. A change in the parameter results in a measurable change in the waveguide. In one embodiment, the change in the applied parameter results in a change in one or more dimension of the waveguide. A dimension of the waveguide is measured. The dimension is converted to the parameter being measured by way of a known relationship. A spring force is applied to the load bearing surface to reduce hysteresis. The spring force can repeatably return the load bearing surface and thereby the dimension of the waveguide to a quiescent condition when unloaded.

In a non-limiting example, the length of the waveguide is measured. A force, load or pressure applied to the contacting surfaces of the load sensing platform modifies the length of the waveguide. A transducer emits one or more energy waves into the waveguide. The transit time, frequency, or phase of the energy wave propagating in the waveguide is measured. The measured transit time, frequency, or phase is converted to a precise length of the waveguide. As disclosed above, the length of the waveguide can then be converted to the applied parameter by calculation through a known length to parameter relationship.

Position where the parameter is applied to the load bearing surfaces can be measured. More than one waveguide is coupled between the load bearing surfaces. In one embodiment, three sensing assemblages are used. The sensing assemblages are located at predetermined positions. Each sensing assemblage measures the parameter. The magnitude and difference of each measurement is compared. The position on the contact surface of the applied parameter is determined by the measurements and difference in measurements of the sensing assemblages in conjunction with the known locations of sensing assemblages. In one embodiment, a spring force is applied around a periphery of the contact surfaces to prevent cantilevering to prevent measurement error.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the claims.

What is claimed is:

1. A load sensing platform comprising:
   a load bearing surface;
   a sensing assemblage coupled to the load bearing surface; and
   at least one spring coupled to the load bearing surface where the at least one spring provides mechanical support for the load bearing surface, where the sensing assemblage measures a parameter applied to the load bearing surface, where the at least one spring prevents cantilevering of the load bearing surface, where the at least one spring is a wave spring, and where the wave spring couples peripherally to the at least one load bearing surface.

2. The platform of claim 1 further including a spring retainer to retain the at least one spring coupled to a predetermined location of the load bearing surface.

3. The platform of claim 1 where the at least one spring has a linear range of displacement over a measurement range of the sensing assemblage.

4. The platform of claim 1 where the load sensing platform detects position of contact on the load bearing surface.

5. The platform of claim 1 where the sensing assemblage comprises:
   at least one transducer; and
   a compressible waveguide.

6. The platform of claim 5 where the sensing assemblage measures a measures a transit time, frequency, or phase of an acoustic energy wave propagating through the compressible waveguide.

7. The platform of claim 6 where the platform measures a parameter of the muscular-skeletal system.

8. The platform of claim 7 where the platform is coupled between a joint of the muscular-skeletal system.

9. A load sensing platform to measure a parameter of the muscular-skeletal system comprising:
- at least one load bearing surface;
- at least one spring retainer;
- at least one spring; and
- a sensing assemblage to measure a parameter and position applied to the at least one load bearing surface where the sensing assemblage is mechanically coupled to the at least one load bearing surface, where the at least one spring retainer maintains a coupling of the at least one spring to a predetermined position on the at least one load bearing surface, and where the sensing assemblage comprises:
    - a single transducer to transmit and receive energy waves;
    - a waveguide where the single transducer is coupled to the waveguide at a first location; and
    - a reflecting feature at a second location of the waveguide where the single transducer emits an energy wave in the waveguide that is reflected by the reflecting feature to produce a reflected energy wave that is detected by the single transducer.

10. The load sensing platform of claim 9, where the at least one spring retainer retains a disc spring coupled to a periphery of the load bearing surface to support and balance the sensing assemblage.

11. The load sensing platform of claim 10 where the waveguide serves as a spring bias.

12. The load sensing platform of claim 9 where the sensing assemblage comprises:
- a first transducer;
- a waveguide; and
the reflecting surface is replaced with a second transducer where the first transducer couples to the waveguide at the first location and the second transducer couples to the waveguide at the second location.

13. A method of measuring a parameter of the muscular-skeletal system:
- applying the parameter to a load bearing surface where a change in the parameter produces a measurable change in one or more dimensions;
- measuring the one or more dimensions;
- converting a measured dimension to the applied parameter;
- applying a spring force to the load bearing surface to reduce hysteresis and return a load bearing surface to a repeatable dimension under quiescent conditions.

14. The method of claim 13 further including the steps of:
- coupling a waveguide to the load bearing surface where a waveguide length changes as a force is applied to the load bearing surface;
- emitting a energy wave into the waveguide;
- measuring one of a transit time, frequency, or phase of the energy wave through the waveguide;
- converting a measured transit time, frequency, or phase to a length of the waveguide; and
- converting the length of the waveguide to the parameter applied to the load bearing surface.

15. The method of claim 13 further including the steps of:
- measuring a change in dimension due to the applied parameter on the load bearing surface at more that one location of the load bearing surface;
- comparing a difference in measured parameters at the more than one location; and
- determining an applied position of the parameter on the load bearing surface from the difference in measured parameters.

16. The method of claim 13 further including a step of applying the spring force around a periphery of the load bearing surface to prevent cantilevering.

* * * * *